United States Patent
Gelernter et al.

(10) Patent No.: US 10,900,082 B2
(45) Date of Patent: Jan. 26, 2021

(54) GENOTYPE-GUIDED DOSING OF OPIOID RECEPTOR AGONISTS

(71) Applicants: Yale University, New Haven, CT (US); The Trustees of the University of Pennsylvania, Philadelphia, PA (US)

(72) Inventors: Joel Gelernter, New Haven, CT (US); Andrew Smith, New Haven, CT (US); Henry R. Kranzler, Philadelphia, PA (US)

(73) Assignees: Yale University, New Haven, CT (US); The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/878,640

(22) Filed: Jan. 24, 2018

(65) Prior Publication Data

US 2018/0216188 A1  Aug. 2, 2018

Related U.S. Application Data

(60) Provisional application No. 62/449,895, filed on Jan. 24, 2017.

(51) Int. Cl.
*C12Q 1/68* (2018.01)
*C12Q 1/6883* (2018.01)
*A61K 31/137* (2006.01)

(52) U.S. Cl.
CPC .......... *C12Q 1/6883* (2013.01); *A61K 31/137* (2013.01); *C12Q 2600/106* (2013.01); *C12Q 2600/156* (2013.01); *C12Q 2600/158* (2013.01)

(58) Field of Classification Search
None
See application file for complete search history.

(56) References Cited

PUBLICATIONS

Aoki et al., Association between the rs1465040 single-nucleotide polymorphism close to the transient receptor potential subfamily C member 3 (TRPC3) gene and postoperative analgesic requirements. J Pharmacol Sci. Mar. 2015;127(3):391-3. doi: 10.1016/j.jphs.2015.02.005. Epub Feb. 9, 2015.
Coller et al., Lack of influence of CYP2D6 genotype on the clearance of (R)-, (S)- and racemic-methadone. Int J Clin Pharmacol Ther. Jul. 2007;45(7):410-7.
Crettol et al., ABCB1 and cytochrome P450 genotypes and phenotypes: influence on methadone plasma levels and response to treatment. Clin Pharmacol Ther. Dec. 2006;80(6):668-81.
Dennis et al., Impact of ABCB1 and CYP2B6 genetic polymorphisms on methadone metabolism, dose and treatment response in patients with opioid addiction: a systematic review and meta-analysis. PLoS One. Jan. 29, 2014;9(1):e86114. doi: 10.1371/journal.pone.0086114. eCollection 2014.
Eap et al., Cytochrome P450 2D6 genotype and methadone steady-state concentrations. J Clin Psychopharmacol. Apr. 2001;21(2):229-34.
Fonesca et al., Contribution of cytochrome P450 and ABCB1 genetic variability on methadone pharmacokinetics, dose requirements, and response. PLoS One. May 12, 2011;6(5):e19527. doi: 10.1371/journal.pone.0019527.
Gelertner et al., Genome-wide association study of alcohol dependence:significant findings in African- and European-Americans including novel risk loci. Mol Psychiatry. Jan. 2014;19(1):41-9. doi: 10.1038/mp.2013.145. Epub Oct. 29, 2013.
Gelertner et al., Genome-wide association study of cocaine dependence and related traits: FAM53B identified as a risk gene. Mol Psychiatry. Jun. 2014;19(6):717-23. doi: 10.1038/mp.2013.99. Epub Aug. 20, 2013.
Gelertner et al., Genome-wide association study of opioid dependence: multiple associations mapped to calcium and potassium pathways. Biol Psychiatry. Jul. 1, 2014;76(1):66-74. doi: 10.1016/j.biopsych.2013.08.034. Epub Oct. 19, 2013.
Gelernter et al., Opioid receptor gene (OPRM1, OPRK1, and OPRD1) variants and response to naltrexone treatment for alcohol dependence: results from the VA Cooperative Study. Alcohol Clin Exp Res. Apr. 2007;31(4):555-63.
Hancock et al., Cis-Expression Quantitative Trait Loci Mapping Reveals Replicable Associations with Heroin Addiction in OPRM1. Biol Psychiatry. Oct. 1, 2015;78(7):474-84. doi: 10.1016/j.biopsych.2015.01.003. Epub Jan. 29, 2015.
Hung et al., Impact of genetic polymorphisms in ABCB1, CYP2B6, OPRM1, ANKK1 and DRD2 genes on methadone therapy in Han Chinese patients. Pharmacogenomics. Nov. 2011;12(11):1525-33. doi: 10.2217/pp. 11.96. Epub Sep. 8, 2011.
Kharasch et al., Methadone Pharmacogenetics: CYP2B6 Polymorphisms Determine Plasma Concentrations, Clearance, and Metabolism. Anesthesiology. Nov. 2015;123(5):1142-53. doi: 10.1097/ALN.0000000000000867.
Nishizawa et al., Genome-wide association study identifies a potent locus associated with human opioid sensitivity. Mol Psychiatry. Jan. 2014;19(1):55-62. doi: 10.1038/mp.2012.164. Epub Nov. 27, 2012.
Schwantes-An et al., Association of the OPRM1 Variant rs1799971 (A118G) with Non-Specific Liability to Substance Dependence in a Collaborative de novo Meta-Analysis of European-Ancestry Cohorts. Behav Genet. Mar. 2016;46(2):151-69. doi: 10.1007/s10519-0159737-3. Epub Sep. 21, 2015.
Siegle et al., Cellular localization and regional distribution of CYP2D6 mRNA and protein expression in human brain. Pharmacogenetics. Apr. 2001;11(3):237-45.

(Continued)

*Primary Examiner* — Jehanne S Sitton
(74) *Attorney, Agent, or Firm* — Wolf, Greenfield & Sacks, P.C.

(57) ABSTRACT

Provided herein, in some aspects, are methods of dosing opioid receptor agonists for treatment of opioid dependence and pain management.

12 Claims, 6 Drawing Sheets

(56) References Cited

PUBLICATIONS

Wang et al., Involvement of CYP3A4, CYP2C8, and CYP2D6 in the metabolism of (R)- and (S)-methadone in vitro. Drug Metab Dispos. Jun. 2003;31(6):742-7.

Yang et al., Genome-Wide Pharmacogenomic Study on Methadone Maintenance Treatment Identifies SNP rs17180299 and Multiple Haplotypes on CYP2B6, SPON1, and GSG1L Associated with Plasma Concentrations of Methadone R- and S-enantiomers in Heroin-Dependent Patients. PLoS Genet. Mar. 24, 2016;12(3):e1005910. doi: 10.1371/journal.pgen.1005910. eCollection Mar. 2016.

Zhang et al., Association between two mu-opioid receptor gene (OPRM1) haplotype blocks and drug or alcohol dependence. Hum Mol Genet. Mar. 15, 2006;15(6):807-19. Epub Feb. 13, 2006.

λ = 1.013

λ = 1.001

GENOTYPE-GUIDED DOSING OF OPIOID RECEPTOR AGONISTS

RELATED APPLICATIONS

This application claims the benefit under 35 U.S.C. § 119(e) of U.S. provisional application No. 62/449,895, filed Jan. 24, 2017, which is incorporated by reference herein in its entirety.

FEDERALLY-SPONSORED RESEARCH

This invention was made with government support under grant numbers RR019895, HG065403, DA018432, DA028909, DA037665, DA012690, DA012849, GM007205, TR000142, AA017535, and AA011330 awarded by the National Institutes of Health. The government has certain rights in the invention.

BACKGROUND

Opioids are efficacious analgesics, but they are also highly addictive and dangerous. In recent years, an epidemic of opioid abuse has led to a quadrupling of the incidence of drug overdoses and deaths.[1] National prescribing guidelines recently announced by the Centers for Diseases Control are intended to curb the excessive clinical use of opioids,[2] and to promote evidence-based therapies for patients who develop OD.[3] Methadone is used to treat opioid dependence (OD), acting as a selective agonist at the μ-opioid receptor encoded by the OPRM1 gene. Determining the optimal dose for methadone maintenance is time-consuming, and currently no biomarkers are available to guide personalized treatment.

SUMMARY

Provided herein is a genome-wide association study (GWAS) of standard (daily) therapeutic methadone dose. Opioid dependence (OD) subjects were recruited as part of a larger case and control study. Drug use and treatment history were assessed with a semi-structured interview. A follow-up study was also conducted using morphine dose data, collected from opioid-naïve tonsillectomy and adenoidectomy patients. The GWAS of methadone dose included 383 African-Americans (AAs) and 1,027 European-Americans (EAs). Morphine dose data were available for 241 AA and 277 EA surgical patients. Self-reported standard methadone dose for OD subjects and recorded morphine dose for pediatric patients with surgical pain were used. In AA OD subjects, a genome-wide significant association was identified between therapeutic methadone dose (mean=68.0 mg, standard deviation (SD)=30.1 mg) and rs73568641 (P=2.8× $10^{-8}$), the nearest gene (306 kilobases) being OPRM1. Each minor C allele corresponded to an additional ~20 mg/day of oral methadone, an effect specific to AAs. No genome-wide significant associations were observed in this study with methadone dose (mean=77.8 mg, SD=33.9 mg) in EAs.

In the independent set of opioid-naïve AA children being treated for surgical pain, rs73568641-C was associated with a higher required dose of morphine (P=3.9× $10^{-2}$). Polymorphisms at genomic loci previously shown to associate in a replicable manner with higher opioid analgesic dose also associated with higher methadone dose in the OD sample (AA and EA: n=1,410, genetic score P=1.3× $10^{-3}$). Genetic variants influencing opioid sensitivity across different clinical settings could contribute to precision pharmacotherapy for pain and addiction, allowing for individualized treatment and safer, more rapid symptom relief.

Some embodiments of the present disclosure provide a method of identifying a clinically-optimal dose of a μ-opioid receptor agonist, antagonist, or mixed agonist/antagonist, the method comprising performing a genotypic analysis on (genotyping) a nucleic acid obtained from a subject dependent on an opioid to identify the presence or absence of at least one C allele of single nucleotide polymorphism (SNP) rs73568641 located on chromosome 6, wherein each C allele identified in the nucleic acid corresponds to a μ-opioid receptor agonist, antagonist or mixed agonist/antagonist dose that is increased by about 20 milligrams (mg) per day (mg/day), relative to a standard therapeutic dose of a μ-opioid receptor agonist, antagonist or mixed agonist/antagonist for treatment of opioid dependence.

Other embodiments of the present disclosure provide a method of prescribing a clinically optimal dose of a μ-opioid receptor agonist, antagonist or mixed agonist/antagonist, the method comprising: (a) performing a genotypic analysis on (genotyping) a nucleic acid obtained from a subject dependent on an opioid to identify the presence or absence of at least one C allele of single nucleotide polymorphism (SNP) rs73568641 located on chromosome 6; and (b) prescribing μ-opioid receptor agonist, antagonist or mixed agonist/antagonist at a dose that is increased by about 20 mg/day for each C allele identified in the nucleic acid, relative to a standard therapeutic dose of a μ-opioid receptor agonist, antagonist or mixed agonist/antagonist for treatment of opioid dependence. In some embodiments, the method comprises prescribing a clinically optimal dose of a μ-opioid receptor agonist, antagonist or mixed agonist/antagonist, the method comprising: (a) performing a genotypic analysis on (genotyping) a nucleic acid obtained from a subject dependent on an opioid; (b) identifying in the nucleic acid the presence or absence of at least one C allele of single nucleotide polymorphism (SNP) rs73568641 located on chromosome 6; and (c) prescribing μ-opioid receptor agonist, antagonist or mixed agonist/antagonist at a dose that is increased by about 20 mg/day for each C allele identified in the nucleic acid of (b), relative to a standard therapeutic dose of a μ-opioid receptor agonist, antagonist or mixed agonist/antagonist for treatment of opioid dependence.

Yet other embodiments of the present disclosure provide a personalized method of treating a subject who is dependent on an opioid, the method comprising: (a) performing a genotypic analysis on (genotyping) a nucleic acid obtained from a subject dependent on an opioid to identify the presence or absence of at least one C allele of single nucleotide polymorphism (SNP) rs73568641 located on chromosome 6; and (b) administering to the subject an effective amount of a μ-opioid receptor agonist, antagonist or mixed agonist/antagonist, wherein the effective amount is increased by about 20 mg/day for each C allele identified in the nucleic acid, relative to a standard therapeutic dose of a μ-opioid receptor agonist, antagonist or mixed agonist/antagonist for treatment of opioid dependence. In some embodiments, the method comprises (a) performing a genotypic analysis on (genotyping) a nucleic acid obtained from a subject dependent on an opioid; (b) identifying in the nucleic acid the presence or absence of at least one C allele of single nucleotide polymorphism (SNP) rs73568641 located on chromosome 6; and (c) administering to the subject an effective amount of a μ-opioid receptor agonist, antagonist or mixed agonist/antagonist that is increased by about 20 mg/day for each C allele identified in the nucleic acid of (b), relative to a standard therapeutic dose of a µ-opioid receptor agonist, antagonist or mixed agonist/antagonist for treatment of opioid dependence.

Still other embodiments of the present disclosure provide a method of identifying a clinically-optimal dose of a µ-opioid receptor agonist, antagonist or mixed agonist/antagonist, the method comprising performing a genotypic analysis on (genotyping) a nucleic acid obtained from a subject having pain (a subject who is in pain) to identify the presence or absence of at least one C allele of single nucleotide polymorphism (SNP) rs73568641 located on chromosome 6, wherein each C allele identified in the nucleic acid corresponds to a µ-opioid receptor agonist, antagonist or mixed agonist/antagonist dose that is increased by about 10 micrograms/kilogram (µg/kg), relative to a standard therapeutic dose of a µ-opioid receptor agonist, antagonist or mixed agonist/antagonist for treatment of pain.

Further embodiments of the present disclosure provide a method of prescribing a clinically optimal dose of a µ-opioid receptor agonist, antagonist or mixed agonist/antagonist, the method comprising: (a) performing a genotypic analysis on (genotyping) a nucleic acid obtained from a subject having pain to identify the presence or absence of at least one C allele of single nucleotide polymorphism (SNP) rs73568641 located on chromosome 6; and (b) prescribing µ-opioid receptor agonist, antagonist or mixed agonist/antagonist at a dose that is increased by about 10 µg/kg for each C allele identified in the nucleic acid, relative to a standard therapeutic dose of a µ-opioid receptor agonist, antagonist or mixed agonist/antagonist for treatment of pain. In some embodiments, the method comprises (a) performing a genotypic analysis on (genotyping) a nucleic acid obtained from a subject having pain; (b) identifying in the nucleic acid the presence or absence of at least one C allele of single nucleotide polymorphism (SNP) rs73568641 located on chromosome 6; and (c) prescribing µ-opioid receptor agonist, antagonist or mixed agonist/antagonist at a dose that is increased by about 10 µg/kg for each C allele identified in the nucleic acid of (b), relative to a standard therapeutic dose of a µ-opioid receptor agonist, antagonist or mixed agonist/antagonist for treatment of pain.

Some embodiments of the present disclosure provide a personalized method of treating a subject who is having pain, the method comprising: (a) performing a genotypic analysis on (genotyping) a nucleic acid obtained from a subject having pain to identify the presence or absence of at least one C allele of single nucleotide polymorphism (SNP) rs73568641 located on chromosome 6; and (b) administering to the subject an effective amount of a µ-opioid receptor agonist, antagonist or mixed agonist/antagonist, wherein the effective amount is increased by about 10 µg/kg for each C allele identified in the nucleic acid, relative to a standard therapeutic dose of a µ-opioid receptor agonist, antagonist or mixed agonist/antagonist for treatment of pain. In some embodiments, the method comprises (a) performing a genotypic analysis on (genotyping) a nucleic acid obtained from a subject having pain; (b) identifying in the nucleic acid the presence or absence of at least one C allele of single nucleotide polymorphism (SNP) rs73568641 located on chromosome 6; and (c) administering to the subject an effective amount of a µ-opioid receptor agonist, antagonist or mixed agonist/antagonist that is increased by about 10 µg/kg for each C allele identified in the nucleic acid of (b), relative to a standard therapeutic dose of a µ-opioid receptor agonist, antagonist or mixed agonist/antagonist for treatment of pain.

Also provided herein are compositions comprising: a nucleic acid obtained from human chromosome 6 of a subject and having at least one C allele of single nucleotide polymorphism (SNP) rs73568641; and genotyping reagents. In some embodiments, the genotyping reagents comprise a nucleic acid probe that specifically binds, or a pair of nucleic acid primers that specifically bind, to nucleotide sequences flanking SNP rs73568641. In some embodiments, the nucleic acid probe binds, or the pair of nucleic acid primers bind, to a region within 5-500 nucleotides upstream and/or downstream of SNP rs73568641. In some embodiments, the nucleic acid probe binds, or the pair of nucleic acid primers bind, to a region within 5-100 nucleotides (e.g., within 5, 10, 20, 30, 40, 50, 60, 70, 80, 90 or 100 nucleotides) upstream and/or downstream of SNP rs73568641. In some embodiments, the genotyping reagents comprise a non-naturally occurring reaction buffer. In some embodiments, the genotyping reagents comprise a polymerase and/or free dNTPs. In some embodiments, the polymerase is a recombinant polymerase.

DETAILED DESCRIPTION

Figure 1:
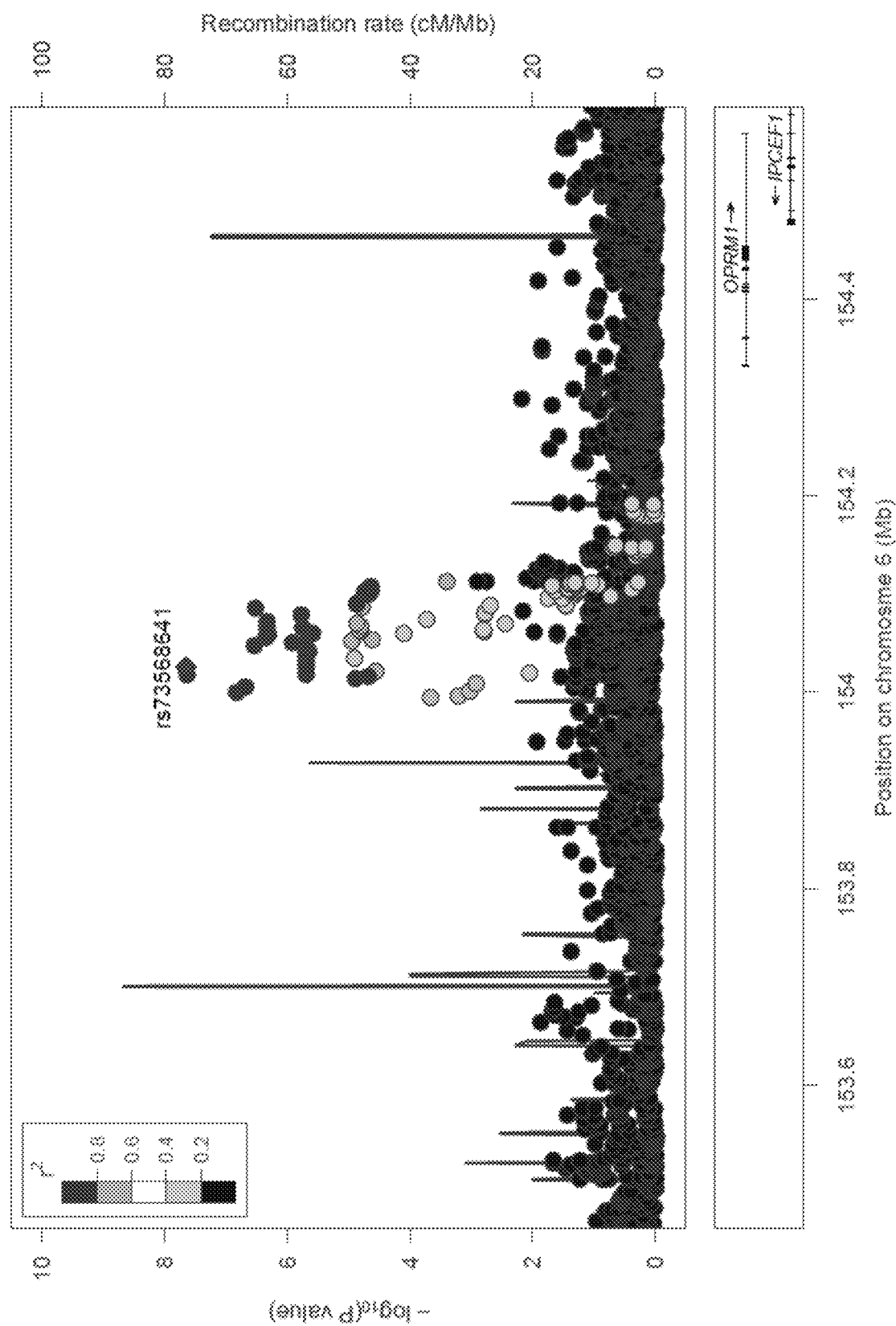
FIG. 1 shows genome-wide significant association with methadone dose in opioid dependent (OD) African-Americans (AAs). Regional association plot of the implicated locus on chromosome 6, showing a genome-wide significant association between methadone dose and single nucleotide polymorphism (SNP) rs73568641 (purple) (AA n=383, P=2.8×10−8). The gene nearest to rs73568641 is OPRM1. Each circle corresponds to a SNP, and the vertical position reflects the $\log_{10}$(P value) (left y-axis). Shading depicts the degree of linkage disequilibrium (r2) between lead SNP rs73568641 and other SNPs in the region. The line indicates the recombination rate (right y-axis). Centimorgan (cM), megabase (Mb).

In methadone-treated opioid dependent (OD) African-Americans (AAs), a single genome-wide association study (GWAS) identified a genome-wide significant association with methadone with the nearest gene being OPRM1. This same SNP was associated with increased morphine dose in an independent sample of AA surgical patients. Consistent with the observation that this SNP's influence is evident across different clinical settings where µ-opioid receptor agonism is employed, top SNPs from prior opioid analgesic dose studies (mapping to three different genomic locations, all separate from OPRM1) were collectively associated with methadone dose in OD patients. These results indicate that the top genetic predictors of opioid dose in the setting of addiction treatment also influence the opioid dose needed to achieve analgesia, and vice-versa.

The observed effect of the rs73568641 minor allele on methadone dose requirements could have immediate clinical utility in the therapeutic dosing of methadone, and perhaps other μ-opioid receptor agonists, in AA patients.

Dosing for Treatment of Opioid Dependence

For decades, the mainstay of evidence-based OD treatment has been the pairing of supportive social services with opioid substitution therapy.[4,5] Methadone is an inexpensive and long-acting synthetic opioid, and like the most frequently abused opioids it is a potent μ-opioid receptor agonist.[6] Methadone maintenance therapy (MMT) is used to treat opioid abuse by reducing craving, withdrawal symptoms, and risk of relapse.[6] The initial, or induction, stage of MMT requires considerable care: excessive methadone doses are dangerous,[7] while overly conservative dosing is ineffective at preventing relapse to illicit opioid use.[8] Determining the clinically optimal dose is time consuming. Methadone dosing must be adjusted based on clinical signs and symptoms, and patients differ greatly in their dose requirements. Despite the clinical challenges posed by methadone administration, and resistance to MMT for social and cultural reasons,[9,10] MMT remains a vitally important treatment strategy for hundreds of thousands of patients in the United States.[11]

Opioids such as methadone and morphine are full agonists at the μ-opioid receptor, which is encoded by the gene OPRM1 on chromosome 6.[6] OPRM1 has been the subject of interest, particularly the common missense single nucleotide polymorphism (SNP) rs1799971, but also non-coding variation, with dozens of candidate gene association studies having examined a wide range of phenotypes.[12-14] Many of the initial claims about associations between the candidate missense variant rs1799971 and clinical phenotypes have not proven to be robust,[15,16] although modest effects do appear to be present.[17,18] In addition to OPRM1, studies have also examined the relationship between methadone metabolism and candidate polymorphisms in genes encoding cytochrome P450 enzymes, including CYP3A4, CYP2B6 and CYP2D6.[19-21] Neither metabolic enzyme polymorphisms nor serum methadone levels (SMLs) have yet been shown to be reliable predictors of maintenance dose.[22,23] Genes related to both pharmacodynamics and pharmacokinetics may, however, influence each individual's dosing needs.

Provided herein, in some embodiments, are methods of identifying a dose, such as a clinically-optimal dose, of a μ-opioid receptor agonist, antagonist or mixed agonist/antagonist for treatment of opioid dependence. The μ-opioid receptors (MOR) are a class of opioid receptors with a high affinity for enkephalins and beta-endorphin, but a low affinity for dynorphins. The prototypical μ-opioid receptor agonist is morphine, the primary psychoactive alkaloid in opium. Examples of "μ-opioid receptor agonists" include, but are not limited to, morphine, levorphanol, cebranopadol, pethidine, fentanyl, buprenorphine (SUBUTEX®), butorphanol, and eluxadoline. In some embodiments, a μ-opioid receptor agonist is morphine, codeine, fentanyl, hydrocodone or hydromorphone or meperidine.

Examples of "μ-opioid receptor antagonists" include, but are not limited to, naloxone (NARCAN®), naltrexone, nalmefene, and nalorphine.

Examples of "μ-opioid receptor mixed agonist/antagonists" include, but are not limited to, a combination of buprenorphine and naloxone (e.g., SUBOXONEμ).

A "clinically optimal dose" may be a dose that provides clinical benefit to a particular subject without causing substantial sedation or substantial respiratory depression.

Methods herein may comprise, for example, performing a genotypic analysis on a nucleic acid (e.g., DNA or RNA) obtained from a subject (e.g., a human subject, such as an African-American subject) dependent on an opioid (e.g., morphine, codeine, fentanyl, hydrocodone or hydromorphone or meperidine) to identify the presence of (e.g., a TC genotype or a CC genotype) or absence of (e.g., a TT genotype) at least one C allele of single nucleotide polymorphism (SNP) rs73568641, located on chromosome 6.

Methods of genotypic nucleic acids (determining nucleic acid sequence) are known and include, for example, molecular tools such as restriction fragment length polymorphism identification (RFLPI) of genomic DNA, random amplified polymorphic detection (RAPD) of genomic DNA, amplified fragment length polymorphism detection (AFLPD), polymerase chain reaction (PCR), DNA sequencing, allele specific oligonucleotide (ASO) probes, and hybridization to DNA microarrays or beads.

Each C allele identified in a nucleic acid (e.g., obtained from a biological sample (e.g., blood sample, of a subject), in some embodiments, corresponds to a μ-opioid receptor agonist dose (e.g., methadone dose) that is increased by (or by about, e.g., within 5% of or within 20% of) 20 milligrams (mg) per day, relative to a standard therapeutic dose of a μ-opioid receptor agonist for treatment of opioid dependence. In some embodiments, each C allele identified in a nucleic acid corresponds to a μ-opioid receptor agonist dose (e.g., methadone dose) that is increased by (or by about) 5, 10, 15, 20, 25 or 30 milligrams (mg) per day.

Also provided herein, in some embodiments, are methods of prescribing a dose, such as a clinically optimal dose, of a μ-opioid receptor agonist, antagonist or mixed agonist/antagonist for treatment of opioid dependence. In some embodiments, the methods comprise: (a) performing a genotypic analysis on a nucleic acid obtained from a subject dependent on an opioid to identify the presence or absence of at least one C allele of single nucleotide polymorphism (SNP) rs73568641 located on chromosome 6; and (b) prescribing μ-opioid receptor agonist, antagonist or mixed agonist/antagonist at a dose that is increased by about 20 milligrams (mg) per day for each C allele identified in the nucleic acid, relative to a standard therapeutic dose of a μ-opioid receptor agonist, antagonist or mixed agonist/antagonist for treatment of opioid dependence. In some embodiments, the methods comprise (a) performing a genotypic analysis on a nucleic acid obtained from a subject dependent on an opioid; (b) identifying in the nucleic acid the presence or absence of at least one C allele of single nucleotide polymorphism (SNP) rs73568641 located on chromosome 6; and (c) prescribing μ-opioid receptor agonist, antagonist or mixed agonist/antagonist at a dose that is increased by about 20 milligrams (mg) per day for each C allele identified in the nucleic acid of (b), relative to a standard therapeutic dose of a μ-opioid receptor agonist, antagonist or mixed agonist/antagonist for treatment of opioid dependence.

Further provided herein, in some embodiments, are personalized methods of treating a subject who is dependent on an opioid. The methods may comprise, for example, (a) performing a genotypic analysis on a nucleic acid obtained from a subject dependent on an opioid to identify the presence or absence of at least one C allele of single nucleotide polymorphism (SNP) rs73568641 located on chromosome 6; and (b) administering to the subject an effective amount of a µ-opioid receptor agonist, antagonist or mixed agonist/antagonist, wherein the effective amount is increased by about 20 milligrams (mg) per day for each C allele identified in the nucleic acid, relative to a standard therapeutic dose of a µ-opioid receptor agonist, antagonist or mixed agonist/antagonist for treatment of opioid dependence. In some embodiments, the methods comprise (a) performing a genotypic analysis on a nucleic acid obtained from a subject dependent on an opioid; (b) identifying in the nucleic acid the presence or absence of at least one C allele of single nucleotide polymorphism (SNP) rs73568641 located on chromosome 6; and (c) administering to the subject an effective amount of a µ-opioid receptor agonist, antagonist or mixed agonist/antagonist that is increased by about 20 milligrams (mg) per day for each C allele identified in the nucleic acid of (b), relative to a standard therapeutic dose of a µ-opioid receptor agonist, antagonist or mixed agonist/antagonist for treatment of opioid dependence.

"Administration" includes, but is not limited to, oral administration and intravenous administrations. Other routes of administration are encompassed by the present disclosure.

A subject is typically a human subject. In some embodiments, the subject is an African-American subject (a subject having African-American heritage/ancestry). In some embodiments, the subject is an European subject (a subject having European heritage/ancestry). In some embodiments, the subject is dependent on an opioid. For example, the subject may have an opioid use disorder. An opioid use disorder is a medical condition characterized by the compulsive use of opioids (despite adverse consequences from continued opioid use) and the development of a withdrawal symptom when use of the opioid stops. An opioid use disorder may involve both an addiction to and dependence on opioids. The subject, in some embodiments, may be undergoing treatment (e.g., methadone treatment) for an addiction to and/or dependence on an opioid. In some embodiments, the opioid is morphine, codeine, fentanyl, hydrocodone, hydromorphone or meperidine.

A standard therapeutic dose (SD) of a µ-opioid receptor agonist, antagonist or mixed agonist/antagonist for the treatment of opioid dependence is the dose mean typically administered to a subject dependent on an opioid. In some embodiments, the SD of a µ-opioid receptor agonist, antagonist or mixed agonist/antagonist for the treatment of opioid dependence is 50-80 mg per day (mg/day). For example, the SD of a µ-opioid receptor agonist, antagonist or mixed agonist/antagonist for the treatment of opioid dependence may be (or may be about) 50, 55, 60, 65, 70, 75 or 80 mg/day. In some embodiments, SD of a µ-opioid receptor agonist, antagonist or mixed agonist/antagonist for the treatment of opioid dependence is 55, 56, 57, 58, 59, 60, 61, 62, 63, 64, 65, 66, 68, 68. 69 or 70 mg/day.

Dosing for Pain Management

Provided herein, in some embodiments, are methods of identifying a dose, such as a clinically-optimal dose, of a µ-opioid receptor agonist for pain management (treatment of pain). As discussed above, examples of "µ-opioid receptor agonists" include, but are not limited to, morphine, levorphanol, cebranopadol, pethidine, fentanyl, buprenorphine, butorphanol, and eluxadoline. In some embodiments, a µ-opioid receptor agonist is morphine, codeine, fentanyl, hydrocodone or hydromorphone or meperidine. In some embodiments, a µ-opioid receptor antagonist is naloxone and naltrexone. In some embodiments, a µ-opioid receptor mixed agonist/antagonist includes buprenorphine and naloxone.

Methods herein may comprise, for example, performing a genotypic analysis on a nucleic acid (e.g., DNA or RNA) obtained from a subject (e.g., a human subject, such as a an African-American pediatric subject) in pain to identify the presence of (e.g., a TC genotype or a CC genotype) or absence of (e.g., a TT genotype) at least one C allele of single nucleotide polymorphism (SNP) rs73568641, located on chromosome 6.

Each C allele identified in a nucleic acid (e.g., obtained from a biological sample (e.g., blood sample, of a subject), in some embodiments, corresponds to a µ-opioid receptor agonist dose (e.g., methadone dose), antagonist dose or mixed agonist/antagonist dose that is increased by (or by about, e.g., within 5% of or within 20% of) 10 micrograms (µg) per kilogram of body weight (kg), relative to a standard therapeutic dose of a µ-opioid receptor agonist, antagonist or mixed agonist/antagonist for treatment of pain (for pain management). In some embodiments, each C allele identified in a nucleic acid corresponds to a µ-opioid receptor agonist dose (e.g., methadone dose), antagonist dose or mixed agonist/antagonist dose that is increased by (or by about) 1, 2, 3, 4, 5, 6, 7, 8, 9, 10, 11, 12, 13, 14 or 15 µg/kg per day.

Also provided herein, in some embodiments, are methods of prescribing a dose, such as a clinically optimal dose, of a µ-opioid receptor agonist, antagonist or mixed agonist/antagonist for pain management. In some embodiments, the methods comprise: (a) performing a genotypic analysis on a nucleic acid obtained from a subject having pain to identify the presence or absence of at least one C allele of single nucleotide polymorphism (SNP) rs73568641 located on chromosome 6; and (b) prescribing µ-opioid receptor agonist, antagonist or mixed agonist/antagonist at a dose that is increased by about 10 µg/kg for each C allele identified in the nucleic acid, relative to a standard therapeutic dose of a µ-opioid receptor agonist, antagonist or mixed agonist/antagonist for treatment of pain. In some embodiments, the methods comprise (a) performing a genotypic analysis on a nucleic acid obtained from a subject having pain; (b) identifying in the nucleic acid the presence or absence of at least one C allele of single nucleotide polymorphism (SNP) rs73568641 located on chromosome 6; and (c)prescribing µ-opioid receptor agonist, antagonist or mixed agonist/antagonist at a dose that is increased by about 10 µg/kg for each C allele identified in the nucleic acid of (b), relative to a standard therapeutic dose of a µ-opioid receptor agonist, antagonist or mixed agonist/antagonist for treatment of pain.

Further provided herein, in some embodiments, are personalized methods of treating a subject having pain. The methods may comprise, for example, (a) performing a genotypic analysis on a nucleic acid obtained from a subject having pain to identify the presence or absence of at least one C allele of single nucleotide polymorphism (SNP) rs73568641 located on chromosome 6; and (b) administering to the subject an effective amount of a µ-opioid receptor agonist, antagonist or mixed agonist/antagonist, wherein the effective amount is increased by about 10 µg/kg for each C allele identified in the nucleic acid, relative to a standard therapeutic dose of a µ-opioid receptor agonist, antagonist or mixed agonist/antagonist for treatment of pain. In some embodiments, the methods comprise (a) performing a genotypic analysis on a nucleic acid obtained from a subject having pain; (b) identifying in the nucleic acid the presence or absence of at least one C allele of single nucleotide polymorphism (SNP) rs73568641 located on chromosome 6; and (c) administering to the subject an effective amount of a μ-opioid receptor agonist, antagonist or mixed agonist/antagonist that is increased by about 10 μg/kg for each C allele identified in the nucleic acid of (b), relative to a standard therapeutic dose of a μ-opioid receptor agonist, antagonist or mixed agonist/antagonist for treatment of pain.

As indicated above, a subject is typically a human subject. In some embodiments, the subject is an African-American subject (a subject having African-American heritage/ancestry). In some embodiments, the subject is a pediatric subject, for example, between the ages of 4 and 18 years. Thus, a subject may be 4, 5, 6, 7, 8, 9, 10, 11, 12, 13, 14, 15, 16, 17 or 18 years old. In some embodiments, a subject is experiencing pain. Multiple forms of pain are encompassed by the present disclosure, including, but not limited to, muscle pain, joint pain, nerve pain and surgical pain (resulting from an incision, for example).

A standard therapeutic dose (SD) of a μ-opioid receptor agonist, antagonist or mixed agonist/antagonist for the treatment of pain (pain management) is the dose mean typically administered to a subject having similar pain being treated. In some embodiments, the SD of a μ-opioid receptor agonist, antagonist or mixed agonist/antagonist for the treatment of pain is 100-130 μg/kg of body weight. For example, the SD of a μ-opioid receptor agonist, antagonist or mixed agonist/antagonist for the treatment of pain may be (or may be about) 100, 105, 110, 115, 120, 125 or 130 μg/kg. In some embodiments, SD of a μ-opioid receptor agonist, antagonist or mixed agonist/antagonist for the treatment of pain is 110, 111, 112, 113, 114, 115, 116, 117, 118, 119 or 120 μg/kg.

EXAMPLES

Genome-wide association studies (GWASs) survey the entire catalog of common genetic variants in a hypothesis-free manner—OPRM1 is one gene of interest. A GWAS was performed, as described below, to identify pharmacogenetic determinants of daily methadone dose in a sample of methadone-treated OD subjects, and the results were compared to morphine dose data from an independent clinical sample being treated for acute pain. In this way, identification and characterization of SNPs that associate with therapeutic opioid dose were investigated, as they could enable personalized treatment of individuals based on their genotype.

The association signal that was identified is far enough upstream from the OPRM1 coding region—about 300 kb for the lead SNP—to have entirely escaped interrogation in previous OPRM1 candidate gene studies.[12] The identified locus is non-coding and its molecular function remains unknown. Mechanistic studies in genetically engineered neural cultures might shed light on how the μ opioid receptor's response to exogenous opioids differs by genotype.[53] The possibility that, although OPRM1 is the closest gene, the association is partially, or even entirely, attributable to cis-effects or trans-effects elsewhere in the genome cannot be ruled out. Genetic variants at loci related to methadone metabolism may also be clinically relevant, but their study has been complicated by the presence of differently metabolized optical isomers,[54] the use of different experimental paradigms,[20,21,55-57] and the possible tissue specificity of enzymatic activity.[58,59]

The GWAS described below is larger than all previously published opioid dose GWASs,[40,44,45,69] and the GS results reinforce that these earlier GWASs were likely successful in identifying real signals despite modest sample sizes. Thus, the larger present sample should be sufficient, especially considering the validation of rs73568641 in an independent sample of morphine-treated patients. Evaluation of rs73568641 using clinically documented morphine dose data further supports the reliability of the reported methadone dose data.[70]

Methadone Dose Genome-Wide Association Study (GWAS) Identifies a Significant Association Upstream of OPRM1 at rs73568641

Figure 2:
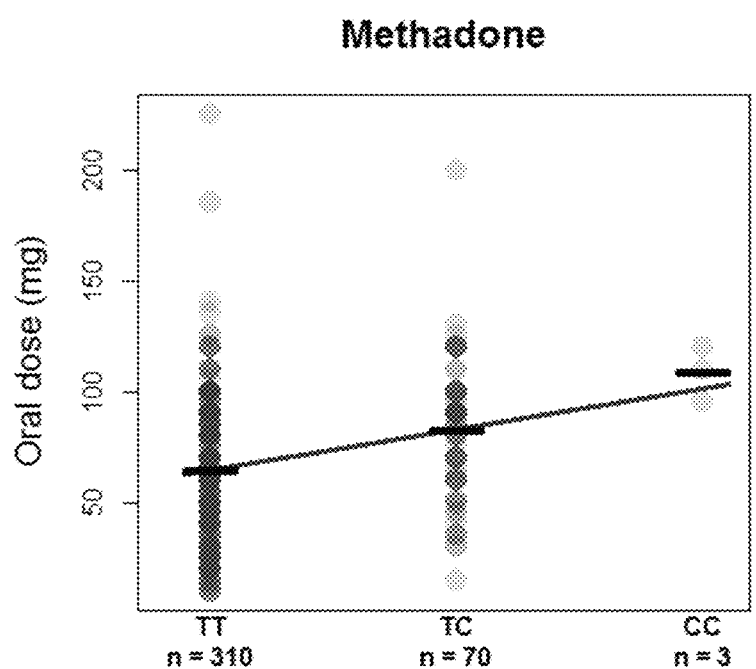
FIG. 2 shows methadone doses stratified by rs73568641 genotype in opioid dependent (OD) African Americans (AAs). Oral methadone dose is shown in milligrams (mg). Bars mark group means. Best fit line are shown.
Figure 4:
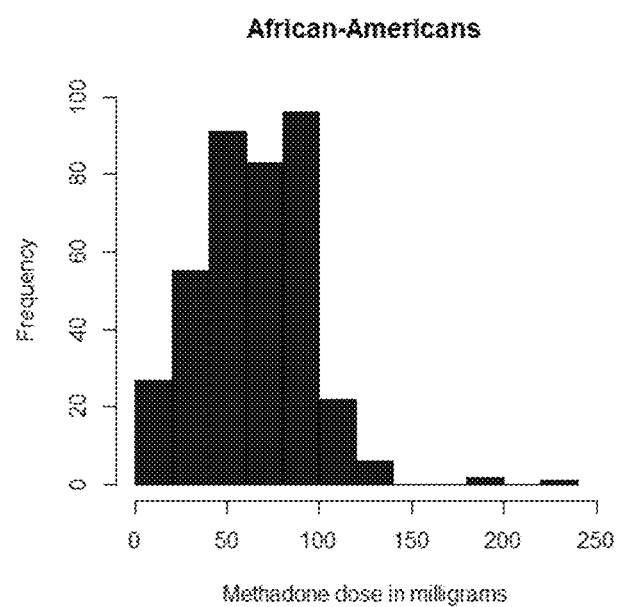
FIG. 4 is a graph depicting methadone dose distribution in African-Americans (AAs).
Figure 5:
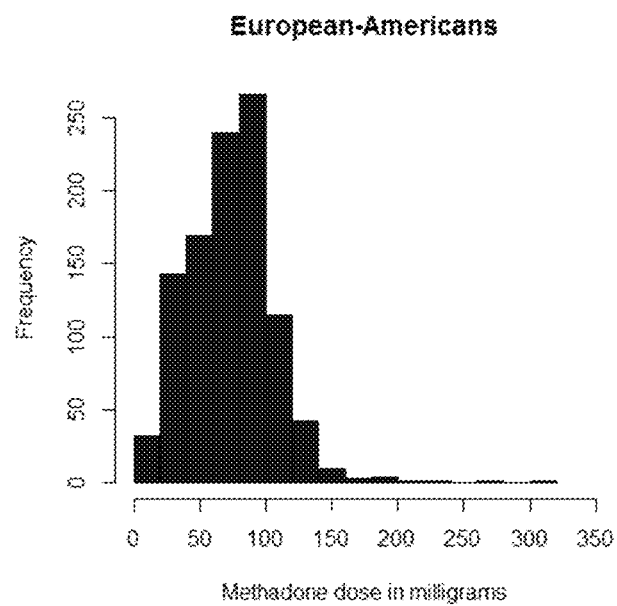
FIG. 5 is a graph depicting methadone dose distribution in European-Americans (EAs).
Figure 6:
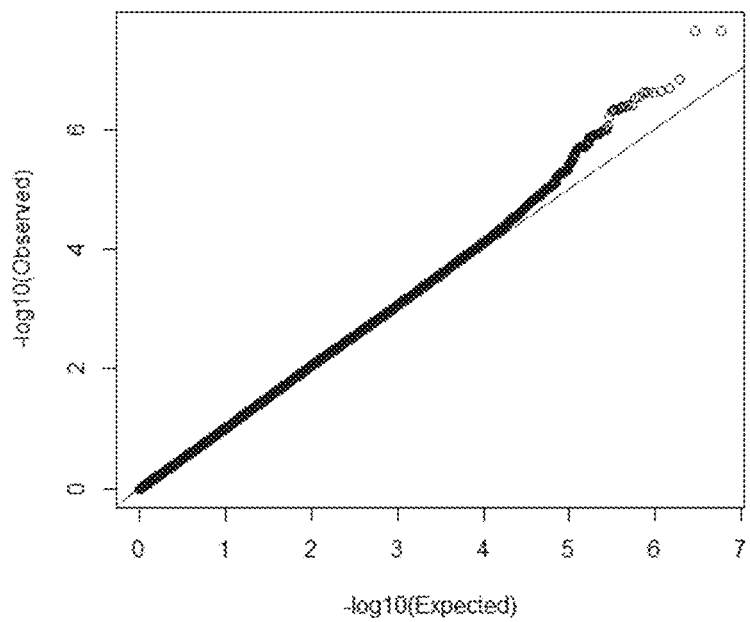
FIG. 6 is a QQ plot from a genome-wide association study (GWAS) in African-Americans (AAs).
Figure 7:
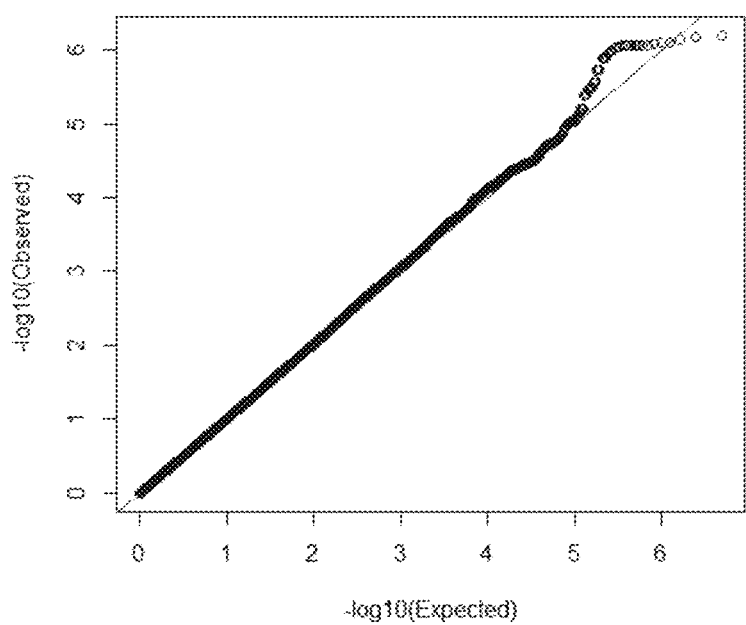
FIG. 7 is a QQ plot from genome-wide association study (GWAS) in European-Americans (EAs).
Figure 8A:
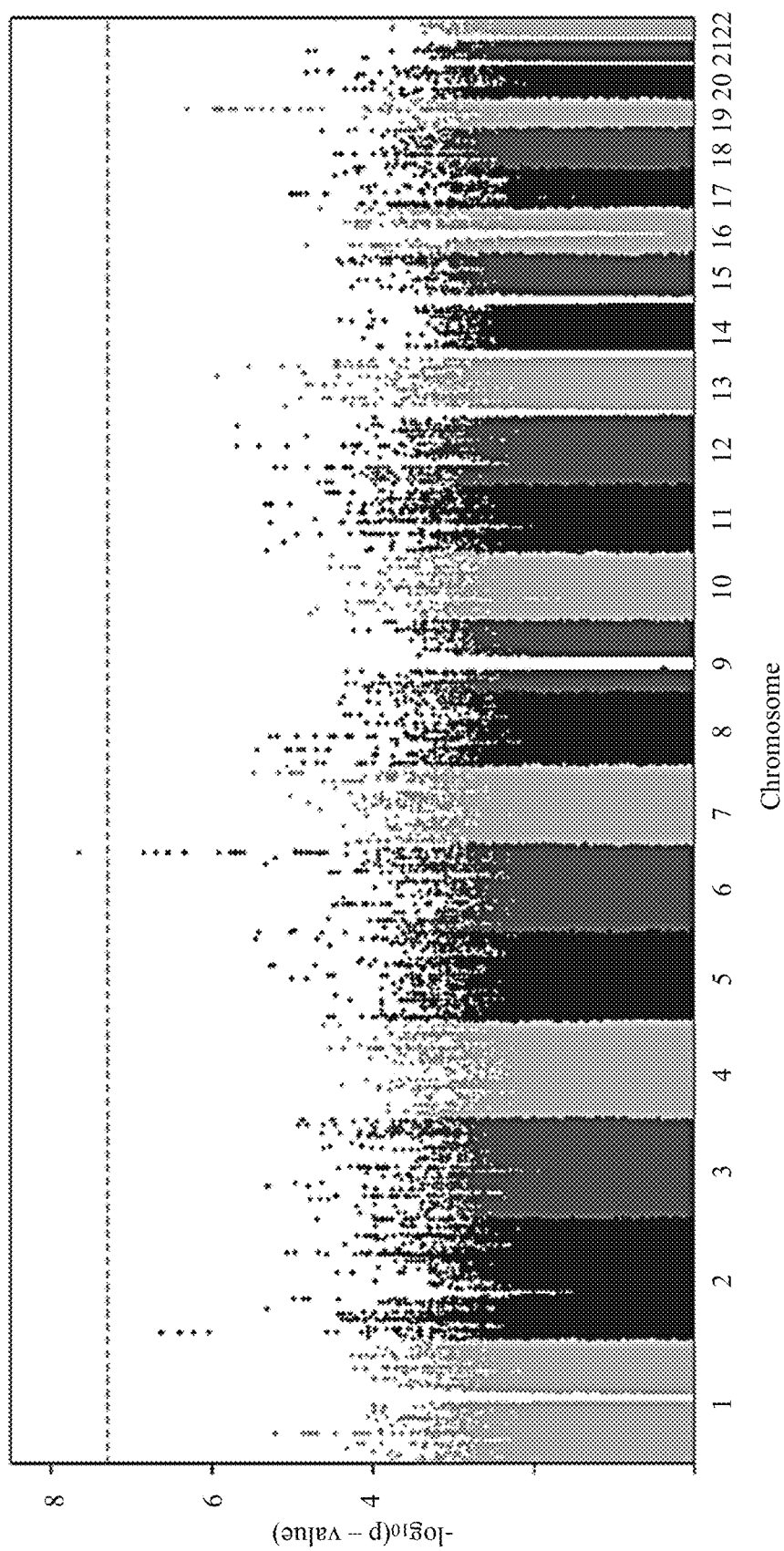
FIGS. 8A-8B show Manhattan plots from methadone dose genome-wide association study in African-Americans (FIG. 8A) and European-Americans (FIG. 8B).
Figure 8B:
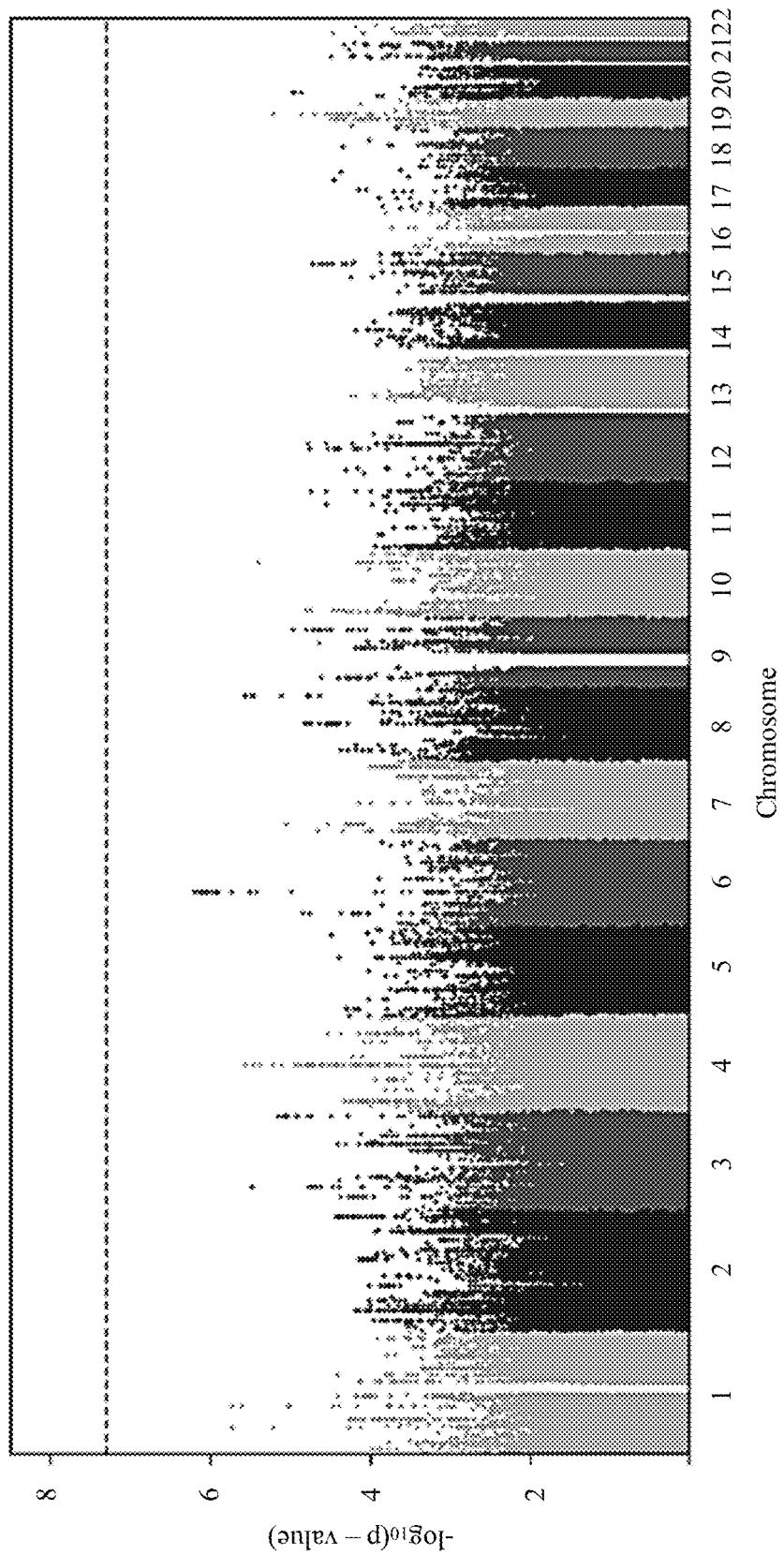

Table 1 provides an overview of sample demographics. Dose data for AAs (mean (standard deviation (SD))=68.0 mg (30.1 mg)) and EAs (mean (SD)=77.8 mg (33.9 mg)) are shown in FIGS. 4 and 5, respectively. The GWAS conducted in AAs identified one genome-wide significant region on chromosome 6 (lead SNP rs73568641, n=383, P=2.3×10$^{-8}$; AA quantile-quantile (QQ) plot is shown in FIG. 6; summary statistics for all SNPs with P<5.0×10$^{-5}$ in AAs are provided in Table 2). Lead SNP rs73568641 tags an association peak approximately ~300 kilobases (kb) upstream of the OPRM1 transcription start site (FIG. 1). In AAs, the minor (C) allele of rs73568641 (MAF=0.1) was associated with a higher daily methadone dose: TT genotype (n=310), dose mean (SD)=64.4 mg (29.8 mg); TC genotype (n=70), dose mean (SD)=82.3 mg (30.1 mg); CC genotype (n=3), dose mean (SD)=108.3 mg (12.6 mg) (FIG. 2). The association between methadone dose and rs73568641 was specific to AAs (EA n=1,027, MAF=0.17, P=0.32), and no SNPs were genome-wide significant in the GWAS conducted in the EA sample (EA QQ plot is shown in FIG. 7; summary statistics for all SNPs with P<5.0×10$^{-5}$ in EAs are provided in Table 3). Manhattan plots are shown in FIG. 8. In an exploratory analysis evaluating previously studied candidate alleles from genes encoding methadone metabolizing enzymes,[43] suggestive evidence that the CYP2D6 loss of function variant rs3892097 is associated with lower methadone dose (AA and EA n=1,410, P=2.6×10$^{-3}$) (Table 4) was found.

TABLE 1

Overview of methadone dose genome-wide association study (GWAS) sample

|  | African-Americans | European-Americans |
|---|---|---|
| Sample size | 383 | 1,027 |
| Men |  |  |
| Subjects, n (%) | 225 (58.8) | 617 (60.1) |
| DSM-IV OD criteria, mean | 6.5 | 6.7 |
| Age, mean (SD), years | 45.6 (8.4) | 37.2 (10.1) |
| Weight, mean (SD), kg | 87.7 (17.3) | 88.0 (17.6) |
| Methadone dose, mean (SD), mg | 66.1 (29.8) | 77.7 (33.1) |
| Women |  |  |
| Subjects, n (%) | 158 (41.3) | 410 (39.9) |
| DSM-IV OD criteria, mean | 6.4 | 6.7 |
| Age, mean (SD), years | 43.0 (7.2) | 37.5 (9.8) |
| Weight, mean (SD), kg | 82.4 (21.9) | 71.5 (16.5) |
| Methadone dose, mean (SD), mg | 70.7 (31.8) | 78.1 (35.1) |

All subjects met criteria for DSM-IV lifetime opioid dependence (OD), had been treated with methadone, and reported their usual daily methadone dose. A maximum of seven DSM-IV OD criteria can be endorsed. Kilograms (kg), milligrams (mg), standard deviation (SD).

TABLE 2

Summary statistics for single nucleotide polymorphisms (SNPs) with P < 5.0 × 10⁻⁵ in African-American (AA) methadone dose genome-wide association studies (GWASs)

| SNP | Chr | Position | A1 | A2 | A1 freq | β | SE | P | Nearest gene | Distance |
|---|---|---|---|---|---|---|---|---|---|---|
| rs73568641 | 6 | 154025139 | C | T | 0.10 | 0.6808 | 0.1226 | 2.81E−08 | OPRM1 | 306492 |
| rs7451325 | 6 | 154016517 | C | T | 0.10 | 0.6807 | 0.1226 | 2.83E−08 | OPRM1 | 315114 |
| rs111559266 | 6 | 153998560 | A | G | 0.10 | 0.6546 | 0.1252 | 1.72E−07 | OPRM1 | 333071 |
| rs76499485 | 6 | 154004364 | A | G | 0.10 | 0.6487 | 0.1257 | 2.48E−07 | OPRM1 | 327267 |
| rs7578347 | 2 | 13121168 | T | C | 0.43 | 0.3926 | 0.0764 | 2.77E−07 | TRIB2 | 238310 |
| rs7578329 | 2 | 13121135 | T | C | 0.43 | 0.3924 | 0.0764 | 2.81E−07 | TRIB2 | 238277 |
| rs13423393 | 2 | 13120763 | T | C | 0.43 | 0.3922 | 0.0764 | 2.85E−07 | TRIB2 | 237905 |
| rs6745283 | 2 | 13120700 | A | T | 0.43 | 0.3923 | 0.0765 | 2.93E−07 | TRIB2 | 237842 |
| rs73568677 | 6 | 154046471 | T | C | 0.09 | 0.6431 | 0.1261 | 3.42E−07 | OPRM1 | 285160 |
| rs116777827 | 6 | 154084534 | T | C | 0.11 | 0.5981 | 0.1176 | 3.64E−07 | OPRM1 | 247097 |
| rs4669899 | 2 | 13121465 | T | C | 0.41 | 0.3928 | 0.0779 | 4.62E−07 | TRIB2 | 238607 |
| rs4669900 | 2 | 13121525 | T | C | 0.41 | 0.3925 | 0.078 | 4.87E−07 | TRIB2 | 238667 |
| rs4669901 | 2 | 13121591 | G | A | 0.41 | 0.393 | 0.0781 | 4.88E−07 | TRIB2 | 238733 |
| rs13397286 | 2 | 13120841 | A | G | 0.42 | 0.3926 | 0.0781 | 5.01E−07 | TRIB2 | 237983 |
| rs12664381 | 6 | 154054500 | T | C | 0.11 | 0.5873 | 0.1171 | 5.26E−07 | OPRM1 | 277131 |
| rs12527630 | 6 | 154064934 | G | A | 0.11 | 0.5868 | 0.1172 | 5.50E−07 | OPRM1 | 266697 |
| rs73570652 | 6 | 154070563 | T | C | 0.11 | 0.5867 | 0.1172 | 5.52E−07 | OPRM1 | 261068 |
| rs12663416 | 6 | 154057383 | T | C | 0.11 | 0.5856 | 0.117 | 5.54E−07 | OPRM1 | 274248 |
| rs12104412 | 19 | 36731058 | T | A | 0.15 | 0.4939 | 0.099 | 6.00E−07 | ZNF146 | 1383 |
| rs57072980 | 2 | 13122014 | T | C | 0.43 | 0.3823 | 0.0772 | 7.36E−07 | TRIB2 | 239156 |
| rs1829624 | 2 | 13113843 | T | C | 0.43 | 0.3746 | 0.0768 | 1.08E−06 | TRIB2 | 230985 |
| rs10412772 | 19 | 36696442 | A | G | 0.14 | 0.4736 | 0.0976 | 1.23E−06 | ZNF565 | intronic |
| rs73612167 | 19 | 36693000 | A | G | 0.14 | 0.4739 | 0.0977 | 1.24E−06 | ZNF565 | intronic |
| rs10419962 | 19 | 36705797 | A | G | 0.14 | 0.4724 | 0.0976 | 1.31E−06 | ZNF146 | UTR5 |
| rs10418472 | 19 | 36723598 | G | C | 0.15 | 0.4713 | 0.0974 | 1.32E−06 | ZNF146 | intronic |
| rs148654454 | 19 | 36701651 | T | C | 0.14 | 0.4736 | 0.098 | 1.36E−06 | ZNF565 | intronic |
| rs1772578 | 13 | 81188248 | G | A | 0.42 | −0.3538 | 0.0733 | 1.38E−06 | SPRY2 | 273162 |
| rs73568685 | 6 | 154049469 | G | A | 0.10 | 0.6071 | 0.1259 | 1.43E−06 | OPRM1 | 282162 |
| rs10415692 | 19 | 36684526 | A | G | 0.15 | 0.4712 | 0.0977 | 1.43E−06 | ZNF565 | intronic |
| rs61326559 | 19 | 36721999 | A | G | 0.15 | 0.4669 | 0.0971 | 1.54E−06 | ZNF146 | intronic |
| rs10414754 | 19 | 36721467 | A | G | 0.15 | 0.4668 | 0.0971 | 1.54E−06 | ZNF146 | intronic |
| rs10414444 | 19 | 36726198 | G | A | 0.15 | 0.4682 | 0.0974 | 1.55E−06 | ZNF146 | intronic |
| rs10419778 | 19 | 36726168 | A | T | 0.15 | 0.4682 | 0.0974 | 1.55E−06 | ZNF146 | intronic |
| rs13345802 | 19 | 36712952 | T | C | 0.15 | 0.4666 | 0.0971 | 1.56E−06 | ZNF146 | intronic |
| rs73570675 | 6 | 154077590 | A | T | 0.10 | 0.5785 | 0.1216 | 1.96E−06 | OPRM1 | 254041 |
| rs73600288 | 19 | 36756938 | T | C | 0.09 | 0.5817 | 0.1224 | 2.01E−06 | ZNF146 | 27263 |
| rs73570627 | 6 | 154064350 | A | T | 0.10 | 0.5783 | 0.1217 | 2.02E−06 | OPRM1 | 267281 |
| rs17084441 | 6 | 154048302 | G | A | 0.11 | 0.5428 | 0.1148 | 2.24E−06 | OPRM1 | 283329 |
| rs12662873 | 6 | 154040810 | T | C | 0.11 | 0.5414 | 0.1146 | 2.29E−06 | OPRM1 | 290821 |
| rs12662881 | 6 | 154040694 | A | G | 0.11 | 0.5414 | 0.1146 | 2.29E−06 | OPRM1 | 290937 |
| rs17084422 | 6 | 154042025 | T | A | 0.11 | 0.5414 | 0.1146 | 2.29E−06 | OPRM1 | 289606 |
| rs17084399 | 6 | 154035144 | G | A | 0.11 | 0.5413 | 0.1146 | 2.30E−06 | OPRM1 | 296487 |
| rs73568635 | 6 | 154024699 | A | G | 0.11 | 0.5413 | 0.1146 | 2.30E−06 | OPRM1 | 306932 |
| rs73568651 | 6 | 154029435 | G | T | 0.11 | 0.5413 | 0.1146 | 2.30E−06 | OPRM1 | 302196 |
| rs10405434 | 19 | 36707678 | T | A | 0.14 | 0.4656 | 0.0985 | 2.31E−06 | ZNF146 | intronic |
| rs1002107 | 12 | 77665094 | C | T | 0.34 | 0.3548 | 0.0752 | 2.38E−06 | E2F7 | 205734 |
| rs1937600 | 6 | 154017197 | C | A | 0.11 | 0.54 | 0.1145 | 2.38E−06 | OPRM1 | 314434 |
| rs12317967 | 12 | 115253038 | T | C | 0.38 | −0.402 | 0.0853 | 2.42E−06 | TBX3 | 131069 |
| rs73568668 | 6 | 154040305 | T | C | 0.11 | 0.5406 | 0.1151 | 2.62E−06 | OPRM1 | 291326 |
| rs113277712 | 6 | 154058824 | G | A | 0.11 | 0.5637 | 0.1207 | 3.01E−06 | OPRM1 | 272807 |
| rs56214452 | 19 | 36694573 | A | G | 0.16 | 0.44 | 0.0945 | 3.24E−06 | ZNF565 | intronic |
| rs3858777 | 13 | 99169671 | C | G | 0.30 | 0.3693 | 0.0794 | 3.32E−06 | STK24 | intronic |
| rs11878240 | 19 | 36711991 | G | A | 0.14 | 0.4564 | 0.0985 | 3.64E−06 | ZNF146 | intronic |
| rs28526168 | 7 | 142467218 | A | T | 0.05 | −0.8405 | 0.182 | 3.87E−06 | PRSS1 | 6291 |
| rs28512272 | 7 | 142467564 | G | T | 0.05 | −0.8404 | 0.182 | 3.88E−06 | PRSS1 | 6637 |
| rs5010454 | 5 | 163521465 | G | A | 0.22 | 0.4428 | 0.096 | 4.01E−06 | MAT2B | 575106 |
| rs2543607 | 8 | 30846883 | C | T | 0.46 | −0.352 | 0.0765 | 4.20E−06 | PURG | 6435 |
| rs4338575 | 12 | 77676890 | C | G | 0.32 | 0.3418 | 0.0744 | 4.33E−06 | E2F7 | 217530 |
| rs7731783 | 5 | 177060312 | C | T | 0.46 | −0.3409 | 0.0743 | 4.46E−06 | B4GALT7 | 22966 |
| rs57994318 | 19 | 36683847 | C | T | 0.15 | 0.4528 | 0.099 | 4.74E−06 | ZNF565 | intronic |
| rs7938889 | 11 | 95964519 | T | C | 0.39 | 0.3338 | 0.0734 | 5.40E−06 | MAML2 | intronic |
| rs799227 | 6 | 133487440 | C | G | 0.23 | 0.4082 | 0.0898 | 5.46E−06 | EYA4 | 75055 |
| rs114685959 | 3 | 60837616 | A | G | 0.06 | 0.7616 | 0.1677 | 5.59E−06 | FHIT | intronic |
| rs11695541 | 2 | 60844310 | C | T | 0.09 | 0.6257 | 0.1378 | 5.61E−06 | BCL11A | 63677 |
| rs9667035 | 11 | 1907653 | T | C | 0.22 | 0.4227 | 0.0931 | 5.63E−06 | LSP1 | intronic |
| rs115735018 | 3 | 60835392 | C | T | 0.06 | 0.7612 | 0.1678 | 5.73E−06 | FHIT | intronic |
| rs116783915 | 3 | 60834444 | T | G | 0.06 | 0.7611 | 0.168 | 5.89E−06 | FHIT | intronic |
| rs12362505 | 11 | 95964802 | C | T | 0.39 | 0.3347 | 0.0739 | 5.90E−06 | MAML2 | intronic |
| rs10765800 | 11 | 95962582 | C | T | 0.39 | 0.3332 | 0.0736 | 5.95E−06 | MAML2 | intronic |
| rs7630746 | 3 | 60833538 | C | T | 0.06 | 0.761 | 0.1681 | 5.99E−06 | FHIT | intronic |
| rs4738399 | 8 | 56607003 | T | G | 0.32 | 0.3543 | 0.0783 | 6.07E−06 | TMEM68 | 44300 |
| rs74920379 | 5 | 110484039 | G | C | 0.22 | −0.4025 | 0.089 | 6.09E−06 | WDR36 | 17839 |
| rs75738991 | 11 | 59999794 | C | A | 0.17 | 0.4681 | 0.1036 | 6.21E−06 | MS4A6A | 47655 |
| rs2028258 | 5 | 110482490 | G | A | 0.22 | −0.3994 | 0.0884 | 6.21E−06 | WDR36 | 16290 |

TABLE 2-continued

Summary statistics for single nucleotide polymorphisms (SNPs) with P < 5.0 × 10⁻⁵
in African-American (AA) methadone dose genome-wide association studies (GWASs)

| SNP | Chr | Position | A1 | A2 | A1 freq | β | SE | P | Nearest gene | Distance |
|---|---|---|---|---|---|---|---|---|---|---|
| rs4237576 | 11 | 95965927 | T | C | 0.39 | 0.339 | 0.0751 | 6.35E−06 | MAML2 | intronic |
| rs28794274 | 19 | 36753295 | A | G | 0.11 | 0.5412 | 0.1201 | 6.59E−06 | ZNF146 | 23620 |
| rs10515419 | 5 | 110481826 | C | A | 0.22 | −0.3998 | 0.0888 | 6.70E−06 | WDR36 | 15626 |
| rs1992676 | 12 | 33288173 | T | C | 0.36 | 0.3408 | 0.0758 | 6.92E−06 | PKP2 | 238393 |
| rs2028259 | 5 | 110482060 | A | G | 0.22 | −0.3991 | 0.0888 | 6.95E−06 | WDR36 | 15860 |
| rs2012694 | 1 | 62587720 | A | G | 0.24 | −0.3672 | 0.0817 | 7.04E−06 | INADL | intronic |
| rs528418 | 6 | 145592272 | G | C | 0.09 | 0.583 | 0.1299 | 7.13E−06 | EPM2A | 354168 |
| rs10092873 | 8 | 56619035 | T | C | 0.35 | −0.3454 | 0.0771 | 7.48E−06 | TMEM68 | 32268 |
| rs112163787 | 7 | 142477646 | A | G | 0.07 | −0.7279 | 0.1629 | 7.85E−06 | PRSS1 | 16719 |
| rs7322911 | 13 | 99138353 | T | C | 0.42 | 0.3246 | 0.0729 | 8.43E−06 | STK24 | intronic |
| rs1453995 | 11 | 21170359 | C | T | 0.38 | −0.3565 | 0.0803 | 9.08E−06 | NELL1 | intronic |
| rs9705479 | 12 | 34648826 | T | A | 0.49 | −0.3593 | 0.081 | 9.25E−06 | ALG10 | 467590 |
| rs9705545 | 12 | 34649225 | T | A | 0.49 | −0.3593 | 0.081 | 9.25E−06 | ALG10 | 467989 |
| rs116112440 | 13 | 20387889 | G | T | 0.06 | 0.708 | 0.1598 | 9.34E−06 | ZMYM5 | 9735 |
| rs73608355 | 19 | 36900062 | T | A | 0.09 | 0.5362 | 0.1211 | 9.52E−06 | ZFP82 | intronic |
| rs73608350 | 19 | 36898619 | G | A | 0.09 | 0.5361 | 0.1211 | 9.55E−06 | ZFP82 | intronic |
| rs2543609 | 8 | 30846306 | A | G | 0.45 | −0.3376 | 0.0763 | 9.67E−06 | PURG | 7012 |
| rs73614528 | 19 | 36910680 | C | T | 0.09 | 0.5349 | 0.1209 | 9.67E−06 | ZFP82 | 1130 |
| rs112608286 | 19 | 36907580 | T | C | 0.09 | 0.5347 | 0.1209 | 9.74E−06 | ZFP82 | intronic |
| rs12994830 | 2 | 171284489 | G | T | 0.13 | −0.5018 | 0.1135 | 9.90E−06 | MYO3B | intronic |
| rs62471583 | 7 | 155048135 | T | C | 0.21 | 0.4207 | 0.0952 | 9.97E−06 | INSIG1 | 41351 |
| rs7961187 | 12 | 77673046 | C | A | 0.33 | 0.328 | 0.0743 | 1.01E−05 | E2F7 | 213686 |
| rs78096559 | 19 | 36721473 | A | G | 0.09 | 0.5390 | 0.1223 | 1.04E−05 | ZNF146 | intronic |
| rs2543611 | 8 | 30842666 | T | A | 0.45 | −0.3401 | 0.0772 | 1.06E−05 | PURG | 10652 |
| rs75870256 | 7 | 142456021 | G | A | 0.05 | −0.7701 | 0.1748 | 1.06E−05 | PRSS1 | 1298 |
| rs562808 | 11 | 95961049 | T | C | 0.41 | 0.3213 | 0.073 | 1.07E−05 | MAML2 | intronic |
| rs11489504 | 7 | 97620778 | A | G | 0.05 | 0.8539 | 0.194 | 1.07E−05 | OCM2 | 1362 |
| rs116091224 | 17 | 29825579 | A | G | 0.09 | −0.5744 | 0.1306 | 1.09E−05 | RAB11FIP4 | intronic |
| rs10040391 | 5 | 177052587 | C | T | 0.47 | −0.3263 | 0.0742 | 1.09E−05 | B4GALT7 | 15241 |
| rs8064536 | 17 | 29826771 | G | A | 0.09 | −0.5729 | 0.1304 | 1.11E−05 | RAB11FIP4 | intronic |
| rs78711927 | 5 | 85824061 | A | G | 0.05 | −0.787 | 0.1792 | 1.12E−05 | COX7C | 89723 |
| rs114618298 | 5 | 85827674 | T | C | 0.05 | −0.7874 | 0.1793 | 1.12E−05 | COX7C | 86110 |
| rs116662132 | 5 | 85826808 | C | T | 0.05 | −0.7873 | 0.1793 | 1.13E−05 | COX7C | 86976 |
| rs75611813 | 7 | 142445255 | C | T | 0.05 | −0.7651 | 0.1742 | 1.13E−05 | PRSS1 | 12064 |
| rs77099771 | 17 | 29833511 | T | C | 0.09 | −0.5727 | 0.1306 | 1.15E−05 | RAB11FIP4 | intronic |
| rs77416463 | 17 | 29833299 | T | A | 0.09 | −0.573 | 0.1307 | 1.16E−05 | RAB11FIP4 | intronic |
| rs75595132 | 17 | 29833688 | T | A | 0.09 | −0.5723 | 0.1306 | 1.17E−05 | RAB11FIP4 | intronic |
| rs6733510 | 2 | 79605324 | C | A | 0.35 | 0.3565 | 0.0813 | 1.17E−05 | CTNNA2 | 134736 |
| rs9969054 | 6 | 1186589 | A | T | 0.06 | −0.7029 | 0.1607 | 1.21E−05 | FOXQ1 | 126086 |
| rs76537953 | 17 | 29834517 | G | A | 0.09 | −0.5707 | 0.1305 | 1.22E−05 | RAB11FIP4 | intronic |
| rs9968942 | 6 | 1186313 | T | C | 0.06 | −0.703 | 0.1608 | 1.23E−05 | FOXQ1 | 126362 |
| rs114977270 | 7 | 142439571 | G | A | 0.05 | −0.7618 | 0.1742 | 1.23E−05 | PRSS1 | 17748 |
| rs12477031 | 2 | 171287677 | C | T | 0.12 | −0.508 | 0.1163 | 1.25E−05 | MYO3B | intronic |
| rs9849591 | 3 | 69274066 | G | A | 0.17 | 0.4374 | 0.1002 | 1.26E−05 | FRMD4B | intronic |
| rs73568694 | 6 | 154050883 | C | A | 0.12 | 0.4844 | 0.1109 | 1.26E−05 | OPRM1 | 280748 |
| rs67026903 | 6 | 158441141 | C | T | 0.31 | 0.3386 | 0.0776 | 1.28E−05 | SYNJ2 | intronic |
| rs183338545 | 8 | 56621409 | T | G | 0.14 | 0.4619 | 0.1059 | 1.29E−05 | TMEM68 | 29894 |
| rs2942104 | 11 | 34874780 | A | C | 0.24 | −0.3743 | 0.0859 | 1.31E−05 | APIP | 29063 |
| rs10111254 | 8 | 30845102 | C | T | 0.45 | −0.3314 | 0.0761 | 1.33E−05 | PURG | 8216 |
| rs138956215 | 17 | 29828610 | T | G | 0.09 | −0.5676 | 0.1304 | 1.34E−05 | RAB11FIP4 | intronic |
| rs113739233 | 7 | 142465929 | A | C | 0.06 | −0.7223 | 0.166 | 1.35E−05 | PRSS1 | 5002 |
| rs2700856 | 3 | 182481982 | T | C | 0.12 | −0.493 | 0.1133 | 1.36E−05 | ATP11B | 29309 |
| rs2687788 | 3 | 182482190 | A | G | 0.12 | −0.4929 | 0.1133 | 1.37E−05 | ATP11B | 29101 |
| rs912337 | 13 | 99141272 | T | C | 0.49 | 0.3039 | 0.07 | 1.40E−05 | STK24 | intronic |
| rs17084394 | 6 | 154033562 | T | A | 0.06 | 0.6703 | 0.1544 | 1.42E−05 | OPRM1 | 298069 |
| rs11882807 | 19 | 36666993 | T | C | 0.14 | 0.4521 | 0.1042 | 1.43E−05 | ZNF565 | 5969 |
| rs8076371 | 17 | 29831837 | G | T | 0.09 | −0.5657 | 0.1305 | 1.45E−05 | RAB11FIP4 | intronic |
| rs2985165 | 13 | 38230282 | G | T | 0.39 | 0.3338 | 0.077 | 1.46E−05 | TRPC4 | intronic |
| rs142086272 | 6 | 154012631 | G | A | 0.13 | 0.4772 | 0.1102 | 1.50E−05 | OPRM1 | 319000 |
| rs73570642 | 6 | 154069117 | A | C | 0.13 | 0.4774 | 0.1103 | 1.51E−05 | OPRM1 | 262514 |
| rs58379059 | 3 | 194115777 | T | C | 0.15 | −0.4686 | 0.1083 | 1.52E−05 | GP5 | UTR3 |
| rs12524666 | 6 | 154088541 | T | A | 0.09 | 0.5517 | 0.1275 | 1.52E−05 | OPRM1 | 243090 |
| rs60913085 | 3 | 194115567 | C | T | 0.15 | −0.4685 | 0.1083 | 1.52E−05 | GP5 | UTR3 |
| rs73572625 | 6 | 154089464 | C | T | 0.09 | 0.5516 | 0.1275 | 1.53E−05 | OPRM1 | 242167 |
| rs112437823 | 7 | 142469262 | T | G | 0.06 | −0.7209 | 0.1667 | 1.53E−05 | PRSS1 | 8335 |
| rs56144534 | 3 | 194115646 | A | C | 0.15 | −0.4684 | 0.1083 | 1.53E−05 | GP5 | UTR3 |
| rs61655400 | 3 | 194115581 | C | T | 0.15 | −0.4683 | 0.1083 | 1.54E−05 | GP5 | UTR3 |
| rs6547233 | 2 | 79605059 | T | C | 0.35 | 0.3519 | 0.0814 | 1.55E−05 | CTNNA2 | 135001 |
| rs112452101 | 3 | 194115177 | C | T | 0.15 | −0.4678 | 0.1083 | 1.57E−05 | GP5 | 371 |
| rs2476188 | 1 | 62575427 | G | A | 0.39 | −0.3165 | 0.0733 | 1.57E−05 | INADL | intronic |
| rs12541928 | 8 | 3536658 | A | C | 0.11 | 0.5187 | 0.1202 | 1.59E−05 | CSMD1 | intronic |
| rs2543603 | 8 | 30848256 | C | T | 0.45 | −0.3293 | 0.0763 | 1.59E−05 | PURG | 5062 |
| rs12865236 | 13 | 86617183 | G | A | 0.10 | 0.5153 | 0.1195 | 1.61E−05 | SLITRK6 | 243700 |
| rs28564444 | 13 | 86614908 | C | T | 0.10 | 0.5152 | 0.1195 | 1.62E−05 | SLITRK6 | 241425 |

TABLE 2-continued

Summary statistics for single nucleotide polymorphisms (SNPs) with P < 5.0 × 10⁻⁵
in African-American (AA) methadone dose genome-wide association studies (GWASs)

| SNP | Chr | Position | A1 | A2 | A1 freq | β | SE | P | Nearest gene | Distance |
|---|---|---|---|---|---|---|---|---|---|---|
| rs73570617 | 6 | 154062194 | C | T | 0.13 | 0.4745 | 0.1103 | 1.70E−05 | OPRM1 | 269437 |
| rs7192758 | 16 | 17201437 | T | C | 0.30 | −0.3805 | 0.0885 | 1.71E−05 | XYLT1 | UTR3 |
| rs12529020 | 6 | 154066022 | T | G | 0.13 | 0.4742 | 0.1103 | 1.72E−05 | OPRM1 | 265609 |
| rs1916264 | 3 | 182497222 | T | C | 0.12 | −0.4854 | 0.1129 | 1.73E−05 | ATP11B | 14069 |
| rs2992158 | 13 | 63904291 | T | C | 0.32 | 0.3287 | 0.0765 | 1.74E−05 | PCDH20 | 1914636 |
| rs10860129 | 12 | 97455311 | G | C | 0.31 | 0.3416 | 0.0795 | 1.74E−05 | NEDD1 | 107842 |
| rs115851856 | 17 | 29833509 | T | C | 0.09 | −0.561 | 0.1307 | 1.76E−05 | RAB11FIP4 | intronic |
| rs114182802 | 5 | 85831679 | C | T | 0.05 | −0.7635 | 0.1779 | 1.77E−05 | COX7C | 82105 |
| rs11052486 | 12 | 33310801 | G | A | 0.36 | 0.3275 | 0.0763 | 1.77E−05 | SYT10 | 217547 |
| rs73570612 | 6 | 154060947 | G | A | 0.13 | 0.4739 | 0.1104 | 1.77E−05 | OPRM1 | 270684 |
| rs2324282 | 13 | 63905104 | G | A | 0.30 | 0.3421 | 0.0797 | 1.78E−05 | PCDH20 | 1915449 |
| rs13039691 | 20 | 50423988 | A | G | 0.18 | 0.4237 | 0.0987 | 1.78E−05 | SALL4 | 4940 |
| rs59022094 | 19 | 36818065 | A | C | 0.09 | 0.5373 | 0.1252 | 1.78E−05 | ZFP14 | 7290 |
| rs59790004 | 19 | 36816226 | T | C | 0.09 | 0.5373 | 0.1252 | 1.78E−05 | ZFP14 | 9129 |
| rs1760461 | 2 | 79605911 | A | G | 0.34 | 0.3412 | 0.0795 | 1.78E−05 | CTNNA2 | 134149 |
| rs146302033 | 3 | 60814479 | T | C | 0.06 | 0.7345 | 0.1712 | 1.79E−05 | FHIT | intronic |
| rs72886241 | 3 | 60815024 | A | T | 0.09 | 0.5923 | 0.1381 | 1.80E−05 | FHIT | intronic |
| rs60965858 | 7 | 83090757 | T | C | 0.11 | −0.5255 | 0.1226 | 1.82E−05 | SEMA3E | intronic |
| rs58878595 | 21 | 32139634 | G | C | 0.39 | −0.3554 | 0.0829 | 1.83E−05 | KRTAP21-1 | 11938 |
| rs12405496 | 1 | 62588357 | T | C | 0.24 | −0.3519 | 0.0821 | 1.83E−05 | INADL | intronic |
| rs6899940 | 6 | 154085465 | C | A | 0.13 | 0.4743 | 0.1107 | 1.84E−05 | OPRM1 | 246166 |
| rs1529077 | 3 | 34544337 | C | T | 0.35 | −0.3457 | 0.0808 | 1.90E−05 | PDCD6IP | 633138 |
| rs10889286 | 1 | 62586098 | T | C | 0.24 | −0.346 | 0.0809 | 1.91E−05 | INADL | intronic |
| rs11811987 | 1 | 62590051 | A | G | 0.24 | −0.3485 | 0.0815 | 1.92E−05 | INADL | intronic |
| rs17123111 | 1 | 62583527 | G | A | 0.24 | −0.3459 | 0.0809 | 1.92E−05 | INADL | intronic |
| rs11259005 | 10 | 14354960 | A | C | 0.13 | 0.4783 | 0.1119 | 1.93E−05 | FRMD4A | intronic |
| rs7418709 | 1 | 62579907 | T | C | 0.24 | −0.3457 | 0.0809 | 1.94E−05 | INADL | exonic |
| rs72641122 | 1 | 62587652 | C | T | 0.24 | −0.3468 | 0.0812 | 1.96E−05 | INADL | intronic |
| rs78292904 | 13 | 63907892 | A | C | 0.29 | 0.3432 | 0.0804 | 1.98E−05 | PCDH20 | 1918237 |
| rs114074667 | 13 | 63909895 | T | C | 0.29 | 0.3431 | 0.0804 | 1.99E−05 | PCDH20 | 1920240 |
| rs61148015 | 19 | 36821771 | A | T | 0.09 | 0.5255 | 0.1232 | 2.00E−05 | ZFP14 | 3584 |
| rs138494790 | 19 | 36835096 | A | G | 0.09 | 0.5254 | 0.1232 | 2.01E−05 | ZFP14 | intronic |
| rs73602377 | 19 | 36839760 | C | G | 0.09 | 0.5254 | 0.1232 | 2.01E−05 | ZFP14 | intronic |
| rs73572679 | 6 | 154101173 | A | C | 0.09 | 0.5473 | 0.1284 | 2.04E−05 | OPRM1 | 230458 |
| rs4930184 | 11 | 66521094 | T | G | 0.08 | −0.6381 | 0.1502 | 2.15E−05 | C11orf80 | intronic |
| rs60332945 | 5 | 110502681 | A | G | 0.20 | −0.3951 | 0.093 | 2.16E−05 | WDR36 | 36481 |
| rs11207904 | 1 | 62587298 | A | G | 0.24 | −0.3449 | 0.0812 | 2.18E−05 | INADL | intronic |
| rs9978835 | 21 | 32134022 | G | A | 0.39 | −0.3526 | 0.0831 | 2.23E−05 | KRTAP21-1 | 6326 |
| rs115159438 | 8 | 5004146 | A | C | 0.25 | −0.3466 | 0.0817 | 2.23E−05 | CSMD1 | 151818 |
| rs7099413 | 10 | 23878235 | T | A | 0.30 | −0.3632 | 0.0857 | 2.24E−05 | KIAA1217 | 105440 |
| rs10103586 | 8 | 56610267 | G | A | 0.47 | 0.3068 | 0.0724 | 2.25E−05 | TMEM68 | 41036 |
| rs10186514 | 2 | 239023528 | T | C | 0.40 | −0.3029 | 0.0715 | 2.25E−05 | ESPNL | intronic |
| rs12517450 | 5 | 163520613 | T | C | 0.21 | 0.391 | 0.0923 | 2.28E−05 | MAT2B | 574254 |
| rs12044746 | 1 | 62580201 | A | G | 0.24 | −0.3423 | 0.0808 | 2.29E−05 | INADL | intronic |
| rs6468457 | 8 | 30640865 | G | T | 0.29 | −0.3988 | 0.0942 | 2.31E−05 | PPP2CB | 2261 |
| rs2070756 | 20 | 56139403 | T | C | 0.09 | 0.5963 | 0.1409 | 2.32E−05 | PCK1 | exonic |
| rs6468456 | 8 | 30640864 | A | C | 0.29 | −0.3982 | 0.0941 | 2.33E−05 | PPP2CB | 2262 |
| rs73572674 | 6 | 154098476 | G | A | 0.09 | 0.5434 | 0.1284 | 2.33E−05 | OPRM1 | 233155 |
| rs4343927 | 6 | 154015085 | T | C | 0.10 | 0.5084 | 0.1202 | 2.34E−05 | OPRM1 | 316546 |
| rs67782761 | 8 | 30642026 | C | T | 0.29 | −0.3981 | 0.0941 | 2.34E−05 | PPP2CB | 1100 |
| rs7580243 | 2 | 171030735 | A | C | 0.38 | −0.3276 | 0.0775 | 2.37E−05 | MYO3B | 3920 |
| rs77319296 | 12 | 3934978 | T | C | 0.15 | 0.4446 | 0.1054 | 2.46E−05 | PARP11 | intronic |
| rs7747684 | 6 | 150454280 | C | T | 0.45 | −0.3121 | 0.074 | 2.46E−05 | PPP1R14C | 9908 |
| rs2956078 | 11 | 34879887 | T | C | 0.24 | −0.3617 | 0.0858 | 2.47E−05 | APIP | 23956 |
| rs7206646 | 16 | 89340504 | A | G | 0.30 | 0.3398 | 0.0806 | 2.51E−05 | ANKRD11 | intronic |
| rs142486166 | 6 | 154106575 | A | T | 0.09 | 0.5412 | 0.1284 | 2.52E−05 | OPRM1 | 225056 |
| rs148895837 | 6 | 154105318 | C | T | 0.09 | 0.5411 | 0.1284 | 2.52E−05 | OPRM1 | 226313 |
| rs1937637 | 6 | 154101847 | A | G | 0.09 | 0.5411 | 0.1284 | 2.52E−05 | OPRM1 | 229784 |
| rs4870224 | 6 | 154104380 | T | C | 0.09 | 0.5411 | 0.1284 | 2.52E−05 | OPRM1 | 227251 |
| rs1529078 | 3 | 34544327 | C | T | 0.35 | −0.3417 | 0.0811 | 2.54E−05 | PDCD6IP | 633128 |
| rs12928649 | 16 | 89333342 | C | T | 0.19 | 0.3644 | 0.0866 | 2.56E−05 | ANKRD11 | 691 |
| rs113195506 | 19 | 36674936 | T | C | 0.14 | 0.4426 | 0.1052 | 2.58E−05 | ZNF565 | intronic |
| rs13228464 | 7 | 69346385 | A | G | 0.20 | 0.3828 | 0.091 | 2.59E−05 | AUTS2 | intronic |
| rs78016214 | 5 | 177062200 | G | A | 0.45 | −0.3182 | 0.0757 | 2.63E−05 | B4GALT7 | 24854 |
| rs4892181 | 18 | 71849249 | T | C | 0.35 | 0.3211 | 0.0764 | 2.64E−05 | TIMM21 | 23045 |
| rs9836282 | 3 | 166742591 | C | T | 0.44 | 0.3117 | 0.0742 | 2.65E−05 | ZBBX | 215486 |
| rs4855366 | 3 | 69272761 | G | A | 0.16 | 0.4294 | 0.1023 | 2.69E−05 | FRMD4B | intronic |
| rs6902181 | 6 | 154052198 | T | C | 0.13 | 0.4628 | 0.1103 | 2.73E−05 | OPRM1 | 279433 |
| rs17679896 | 4 | 185128095 | C | T | 0.22 | −0.3863 | 0.0921 | 2.74E−05 | ENPP6 | intronic |
| rs12541559 | 8 | 4994167 | G | C | 0.25 | −0.3504 | 0.0835 | 2.74E−05 | CSMD1 | 141839 |
| rs10005433 | 4 | 185125620 | A | C | 0.22 | −0.3951 | 0.0942 | 2.75E−05 | ENPP6 | intronic |
| rs2872904 | 3 | 182492546 | C | A | 0.12 | −0.4744 | 0.1131 | 2.75E−05 | ATP11B | 18745 |
| rs74932566 | 7 | 126412417 | T | C | 0.07 | 0.6063 | 0.1447 | 2.77E−05 | GRM8 | intronic |
| rs6776838 | 3 | 182489502 | A | T | 0.12 | −0.4737 | 0.113 | 2.78E−05 | ATP11B | 21789 |

TABLE 2-continued

Summary statistics for single nucleotide polymorphisms (SNPs) with $P < 5.0 \times 10^{-5}$
in African-American (AA) methadone dose genome-wide association studies (GWASs)

| SNP | Chr | Position | A1 | A2 | A1 freq | β | SE | P | Nearest gene | Distance |
|---|---|---|---|---|---|---|---|---|---|---|
| rs6443831 | 3 | 182491434 | G | T | 0.12 | −0.4741 | 0.1131 | 2.79E−05 | ATP11B | 19857 |
| rs9843121 | 3 | 182493728 | G | C | 0.12 | −0.4745 | 0.1132 | 2.79E−05 | ATP11B | 17563 |
| rs1112103 | 3 | 182491062 | C | A | 0.12 | −0.474 | 0.1131 | 2.80E−05 | ATP11B | 20229 |
| rs2992155 | 13 | 63903168 | T | C | 0.32 | 0.3205 | 0.0765 | 2.80E−05 | PCDH20 | 1913513 |
| rs2992156 | 13 | 63904050 | T | C | 0.32 | 0.3205 | 0.0765 | 2.80E−05 | PCDH20 | 1914395 |
| rs4859242 | 3 | 182496141 | T | C | 0.12 | −0.4748 | 0.1133 | 2.80E−05 | ATP11B | 15150 |
| rs142182482 | 3 | 138886194 | C | G | 0.16 | 0.4166 | 0.0995 | 2.80E−05 | PRR23C | 122460 |
| rs9603243 | 13 | 38228423 | A | G | 0.40 | 0.3204 | 0.0765 | 2.81E−05 | TRPC4 | intronic |
| rs79514416 | 17 | 29833211 | G | A | 0.10 | −0.5262 | 0.1258 | 2.89E−05 | RAB11FIP4 | intronic |
| rs4331469 | 2 | 170048885 | C | A | 0.49 | 0.3155 | 0.0755 | 2.93E−05 | LRP2 | intronic |
| rs114290776 | 17 | 29833754 | T | A | 0.10 | −0.5251 | 0.1257 | 2.96E−05 | RAB11FIP4 | intronic |
| rs2992154 | 13 | 63903082 | T | C | 0.32 | 0.3195 | 0.0765 | 2.96E−05 | PCDH20 | 1913427 |
| rs8068472 | 17 | 29833925 | G | T | 0.10 | −0.5247 | 0.1257 | 3.00E−05 | RAB11FIP4 | intronic |
| rs9669570 | 12 | 34605425 | A | G | 0.48 | 0.3272 | 0.0784 | 3.01E−05 | ALG10 | 424189 |
| rs77168957 | 12 | 3922145 | A | T | 0.11 | 0.4708 | 0.1128 | 3.02E−05 | PARP11 | intronic |
| rs3225 | 11 | 120100520 | C | G | 0.37 | −0.3248 | 0.0779 | 3.06E−05 | OAF | UTR3 |
| rs64468455 | 8 | 30630150 | T | G | 0.28 | −0.4003 | 0.096 | 3.07E−05 | UBXN8 | 5630 |
| rs78278801 | 6 | 154020050 | G | C | 0.07 | 0.6017 | 0.1443 | 3.07E−05 | OPRM1 | 311581 |
| rs7590964 | 2 | 13126278 | G | A | 0.45 | 0.3188 | 0.0765 | 3.08E−05 | TRIB2 | 243420 |
| rs9706400 | 12 | 34608613 | T | C | 0.48 | 0.3271 | 0.0785 | 3.10E−05 | ALG10 | 427377 |
| rs9669387 | 12 | 34582247 | T | G | 0.48 | 0.3265 | 0.0784 | 3.13E−05 | ALG10 | 401011 |
| rs12520421 | 5 | 9763488 | A | G | 0.21 | −0.4076 | 0.0979 | 3.16E−05 | TAS2R1 | 133025 |
| rs2025406 | 13 | 38236308 | A | G | 0.39 | 0.315 | 0.0757 | 3.17E−05 | TRPC4 | intronic |
| rs10062931 | 5 | 90584636 | T | C | 0.22 | 0.3862 | 0.0928 | 3.17E−05 | ARRDC3 | 79905 |
| rs10955042 | 8 | 30631541 | T | A | 0.28 | −0.3987 | 0.0958 | 3.18E−05 | UBXN8 | 7021 |
| rs74724628 | 6 | 22073225 | T | A | 0.09 | −0.5585 | 0.1343 | 3.20E−05 | PRL | 214248 |
| rs2008163 | 3 | 34544785 | A | G | 0.35 | −0.3293 | 0.0792 | 3.23E−05 | PDCD6IP | 633586 |
| rs7487736 | 12 | 34565361 | T | C | 0.48 | 0.3259 | 0.0784 | 3.24E−05 | ALG10 | 384125 |
| rs7829034 | 8 | 30630062 | T | C | 0.28 | −0.4011 | 0.0965 | 3.25E−05 | UBXN8 | 5542 |
| rs2845708 | 11 | 120105099 | A | T | 0.07 | −0.6064 | 0.146 | 3.26E−05 | POU2F3 | 2250 |
| rs29836 | 5 | 151509649 | G | T | 0.41 | −0.3136 | 0.0755 | 3.27E−05 | GLRA1 | 205252 |
| rs7663911 | 4 | 137522629 | A | G | 0.33 | 0.3268 | 0.0787 | 3.30E−05 | PCDH18 | 917444 |
| rs115620831 | 20 | 56125502 | T | C | 0.06 | 0.6407 | 0.1544 | 3.34E−05 | PCK1 | 10635 |
| rs2281858 | 10 | 105271890 | T | C | 0.35 | −0.3216 | 0.0775 | 3.34E−05 | NEURL1 | intronic |
| rs34320136 | 6 | 115456396 | C | T | 0.18 | 0.3926 | 0.0946 | 3.34E−05 | FRK | 806297 |
| rs7670546 | 4 | 137523572 | T | G | 0.33 | 0.3266 | 0.0787 | 3.34E−05 | PCDH18 | 916501 |
| rs9705975 | 12 | 34603582 | T | A | 0.48 | 0.3266 | 0.0787 | 3.34E−05 | ALG10 | 422346 |
| rs11697993 | 20 | 56127458 | G | C | 0.06 | 0.6406 | 0.1544 | 3.35E−05 | PCK1 | 8679 |
| rs10883877 | 10 | 105266370 | A | G | 0.34 | −0.3236 | 0.078 | 3.35E−05 | NEURL1 | intronic |
| rs11698759 | 20 | 56123169 | C | G | 0.06 | 0.6408 | 0.1545 | 3.37E−05 | PCK1 | 12968 |
| rs11698804 | 20 | 56123367 | A | G | 0.06 | 0.6408 | 0.1545 | 3.37E−05 | PCK1 | 12770 |
| rs9603244 | 13 | 38234369 | T | A | 0.40 | 0.3176 | 0.0766 | 3.38E−05 | TRPC4 | intronic |
| rs13040599 | 20 | 50425764 | A | G | 0.18 | 0.4148 | 0.1001 | 3.39E−05 | SALL4 | 6716 |
| rs141631841 | 3 | 138913911 | T | G | 0.11 | 0.4818 | 0.1163 | 3.41E−05 | MRPS22 | 148950 |
| rs12548322 | 8 | 56639386 | T | A | 0.42 | 0.3078 | 0.0743 | 3.42E−05 | TMEM68 | 11917 |
| rs111709221 | 3 | 194115248 | G | A | 0.13 | −0.4721 | 0.1139 | 3.43E−05 | GP5 | 300 |
| rs9739871 | 12 | 34618917 | A | C | 0.50 | −0.3365 | 0.0812 | 3.44E−05 | ALG10 | 437681 |
| rs17836387 | 12 | 3913946 | T | G | 0.11 | 0.4685 | 0.1131 | 3.46E−05 | PARP11 | 4081 |
| rs2386830 | 10 | 129140763 | G | A | 0.27 | 0.3597 | 0.0869 | 3.46E−05 | DOCK1 | intronic |
| rs1295019 | 11 | 120098044 | A | C | 0.37 | −0.3228 | 0.0781 | 3.59E−05 | OAF | intronic |
| rs8123474 | 20 | 56124582 | A | G | 0.06 | 0.6526 | 0.1579 | 3.60E−05 | PCK1 | 11555 |
| rs2017590 | 6 | 115457968 | C | T | 0.18 | 0.3909 | 0.0946 | 3.61E−05 | FRK | 804725 |
| rs934346 | 6 | 115457895 | C | T | 0.18 | 0.3909 | 0.0946 | 3.61E−05 | FRK | 804798 |
| rs183026200 | 6 | 51094956 | A | C | 0.10 | −0.5801 | 0.1404 | 3.61E−05 | TFAP2B | 279630 |
| rs58125485 | 5 | 90587987 | T | G | 0.23 | 0.3753 | 0.0909 | 3.65E−05 | ARRDC3 | 76554 |
| rs111343836 | 3 | 194115098 | G | A | 0.14 | −0.4534 | 0.1098 | 3.65E−05 | GP5 | 450 |
| rs80278035 | 7 | 126417540 | A | T | 0.07 | 0.5947 | 0.144 | 3.65E−05 | GRM8 | intronic |
| rs73599166 | 8 | 56615539 | G | A | 0.14 | 0.4275 | 0.1036 | 3.67E−05 | TMEM68 | 35764 |
| rs2214018 | 5 | 9748135 | T | C | 0.20 | −0.4089 | 0.0992 | 3.72E−05 | TAS2R1 | 117672 |
| rs2177294 | 3 | 182497755 | C | T | 0.12 | −0.4644 | 0.1126 | 3.74E−05 | ATP11B | 13536 |
| rs11053292 | 12 | 34584499 | C | A | 0.43 | −0.3178 | 0.0771 | 3.76E−05 | ALG10 | 403263 |
| rs2845706 | 11 | 120101780 | A | G | 0.38 | −0.3229 | 0.0784 | 3.83E−05 | OAF | 1130 |
| rs10264003 | 7 | 113837101 | T | C | 0.15 | 0.4464 | 0.1084 | 3.83E−05 | FOXP2 | 217951 |
| rs73405695 | 18 | 27226088 | C | T | 0.06 | −0.6437 | 0.1563 | 3.83E−05 | DSC3 | 1343243 |
| rs9517317 | 13 | 99125711 | G | C | 0.47 | −0.2897 | 0.0704 | 3.83E−05 | STK24 | intronic |
| rs72757859 | 5 | 53617848 | A | T | 0.27 | 0.3352 | 0.0814 | 3.85E−05 | ARL15 | 11445 |
| rs11653085 | 17 | 66784255 | T | C | 0.18 | −0.413 | 0.1004 | 3.87E−05 | ABCA8 | 79173 |
| rs9588218 | 13 | 111306439 | A | G | 0.10 | 0.4862 | 0.1182 | 3.89E−05 | CARS2 | intronic |
| rs73599174 | 8 | 56619945 | A | T | 0.14 | 0.4257 | 0.1035 | 3.89E−05 | TMEM68 | 31358 |
| rs17055760 | 3 | 41373677 | T | C | 0.29 | 0.3441 | 0.0836 | 3.90E−05 | ULK4 | intronic |
| rs41322045 | 13 | 63932387 | A | G | 0.29 | 0.3337 | 0.0811 | 3.91E−05 | PCDH20 | 1942732 |
| rs5766175 | 22 | 45301457 | C | T | 0.35 | 0.3283 | 0.0798 | 3.91E−05 | PHF21B | intronic |
| rs12470058 | 2 | 13125418 | G | A | 0.45 | 0.3167 | 0.077 | 3.91E−05 | TRIB2 | 242560 |
| rs2984822 | 1 | 62562578 | T | C | 0.40 | −0.3084 | 0.075 | 3.92E−05 | INADL | intronic |

TABLE 2-continued

Summary statistics for single nucleotide polymorphisms (SNPs) with P < 5.0 × 10⁻⁵ in African-American (AA) methadone dose genome-wide association studies (GWASs)

| SNP | Chr | Position | A1 | A2 | A1 freq | β | SE | P | Nearest gene | Distance |
|---|---|---|---|---|---|---|---|---|---|---|
| rs12210278 | 6 | 54510342 | C | T | 0.10 | 0.5102 | 0.1241 | 3.95E−05 | FAM83B | 201227 |
| rs13324937 | 3 | 41373912 | G | A | 0.29 | 0.3433 | 0.0835 | 3.98E−05 | ULK4 | intronic |
| rs75492117 | 13 | 111303240 | T | A | 0.10 | 0.4864 | 0.1184 | 3.98E−05 | CARS2 | intronic |
| rs16847409 | 2 | 133843623 | T | C | 0.11 | 0.4946 | 0.1204 | 3.99E−05 | NCKAP5 | intronic |
| rs13321626 | 3 | 41373823 | C | T | 0.29 | 0.3432 | 0.0835 | 4.00E−05 | ULK4 | intronic |
| rs67278599 | 3 | 41373660 | C | T | 0.29 | 0.3432 | 0.0835 | 4.00E−05 | ULK4 | intronic |
| rs77772414 | 13 | 111308875 | T | G | 0.10 | 0.4857 | 0.1183 | 4.02E−05 | CARS2 | intronic |
| rs10176860 | 2 | 133841981 | C | T | 0.11 | 0.4926 | 0.1201 | 4.10E−05 | NCKAP5 | intronic |
| rs9584856 | 13 | 99126551 | G | T | 0.47 | −0.2869 | 0.07 | 4.12E−05 | STK24 | intronic |
| rs11854174 | 15 | 88285061 | C | T | 0.39 | 0.3071 | 0.0749 | 4.12E−05 | NTRK3 | 134927 |
| rs6709902 | 2 | 79606988 | A | G | 0.46 | 0.305 | 0.0744 | 4.13E−05 | CTNNA2 | 133072 |
| rs10219775 | 13 | 111340522 | A | G | 0.10 | 0.494 | 0.1205 | 4.13E−05 | CARS2 | intronic |
| rs35109791 | 6 | 115437721 | G | A | 0.18 | 0.3878 | 0.0946 | 4.16E−05 | FRK | 824972 |
| rs7595364 | 2 | 48842236 | T | C | 0.15 | 0.4512 | 0.1101 | 4.18E−05 | STON1-GTF2A1L | intronic |
| rs9645891 | 13 | 99126800 | A | G | 0.47 | −0.2874 | 0.0702 | 4.20E−05 | STK24 | intronic |
| rs10219862 | 13 | 111341628 | G | C | 0.10 | 0.4939 | 0.1206 | 4.21E−05 | CARS2 | intronic |
| rs34900644 | 6 | 115439760 | C | T | 0.18 | 0.3873 | 0.0946 | 4.26E−05 | FRK | 822933 |
| rs505142 | 11 | 120098746 | A | T | 0.37 | −0.3201 | 0.0782 | 4.27E−05 | OAF | intronic |
| rs34429532 | 3 | 98125954 | T | C | 0.30 | 0.3386 | 0.0827 | 4.27E−05 | OR5K3 | 15479 |
| rs76967190 | 15 | 90856021 | C | A | 0.18 | −0.4205 | 0.1028 | 4.29E−05 | ZNF774 | 39456 |
| rs1419333 | 13 | 81187928 | C | G | 0.34 | −0.3113 | 0.0761 | 4.30E−05 | SPRY2 | 272842 |
| rs8018802 | 14 | 78129834 | T | C | 0.31 | 0.3444 | 0.0843 | 4.36E−05 | ALKBH1 | 8915 |
| rs12681237 | 8 | 122145935 | C | T | 0.38 | 0.317 | 0.0776 | 4.42E−05 | SNTB1 | 321626 |
| rs55780913 | 3 | 166465594 | C | T | 0.49 | 0.326 | 0.0798 | 4.43E−05 | ZBBX | 492483 |
| rs2310000 | 4 | 185127194 | T | A | 0.21 | −0.3803 | 0.0932 | 4.51E−05 | ENPP6 | intronic |
| rs111999863 | 18 | 27221601 | G | C | 0.06 | −0.631 | 0.1547 | 4.54E−05 | DSC3 | 1347730 |
| rs73405682 | 18 | 27221917 | G | C | 0.06 | −0.6314 | 0.1548 | 4.54E−05 | DSC3 | 1347414 |
| rs3112210 | 2 | 39029532 | T | C | 0.36 | −0.312 | 0.0765 | 4.54E−05 | DHX57 | intronic |
| rs2986059 | 10 | 105272025 | A | G | 0.35 | −0.3203 | 0.0786 | 4.62E−05 | NEURL1 | intronic |
| rs8029316 | 15 | 82156415 | T | C | 0.45 | 0.3256 | 0.0799 | 4.63E−05 | MEX3B | 177704 |
| rs73821167 | 4 | 65243796 | A | T | 0.07 | 0.5661 | 0.139 | 4.66E−05 | TECRL | intronic |
| rs79822856 | 18 | 27215262 | T | A | 0.06 | −0.6272 | 0.1541 | 4.71E−05 | DSC3 | 1354069 |
| rs114389064 | 11 | 59677729 | T | C | 0.07 | 0.6264 | 0.154 | 4.76E−05 | TCN1 | 43688 |
| rs7452783 | 6 | 65367463 | A | C | 0.41 | −0.3179 | 0.0782 | 4.81E−05 | EYS | intronic |
| rs35817922 | 12 | 76608154 | A | C | 0.17 | −0.3997 | 0.0983 | 4.82E−05 | NAP1L1 | 129341 |
| rs10844487 | 12 | 33319964 | T | C | 0.45 | 0.3236 | 0.0796 | 4.82E−05 | SYT10 | 208384 |
| rs9474942 | 6 | 54507616 | A | C | 0.10 | 0.504 | 0.124 | 4.82E−05 | FAM83B | 203953 |
| rs74614114 | 7 | 126497016 | G | T | 0.08 | 0.5499 | 0.1354 | 4.87E−05 | GRM8 | intronic |
| rs4736662 | 8 | 134398689 | G | T | 0.33 | 0.3172 | 0.0781 | 4.89E−05 | ST3GAL1 | 68402 |
| rs75385025 | 13 | 35175779 | T | C | 0.05 | −0.7018 | 0.1728 | 4.90E−05 | NBEA | 340645 |
| rs34469803 | 12 | 76607901 | A | T | 0.17 | −0.3989 | 0.0982 | 4.90E−05 | NAP1L1 | 129088 |
| rs11543632 | 7 | 36971130 | T | C | 0.19 | −0.3993 | 0.0983 | 4.91E−05 | ELMO1 | intronic |
| rs78765570 | 11 | 59687612 | A | G | 0.07 | 0.6256 | 0.1541 | 4.92E−05 | TCN1 | 53571 |
| rs8180339 | 4 | 137525549 | T | G | 0.33 | 0.3232 | 0.0796 | 4.93E−05 | PCDH18 | 914524 |
| rs9668744 | 12 | 34624008 | A | C | 0.48 | 0.3235 | 0.0797 | 4.93E−05 | ALG10 | 442772 |
| rs7309929 | 12 | 78177673 | G | T | 0.44 | −0.2839 | 0.07 | 4.95E−05 | NAV3 | 47396 |
| rs9705521 | 12 | 34622961 | T | C | 0.48 | 0.3235 | 0.0797 | 4.96E−05 | ALG10 | 441725 |
| rs1156466 | 2 | 50952775 | C | G | 0.09 | 0.5228 | 0.1288 | 4.96E−05 | NRXN1 | intronic |

TABLE 3

Summary statistics for single nucleotide polymorphisms (SNPs) with P < 5.0 × 10⁻⁵ in European-American (EA) methadone dose genome-wide association studies (GWASs)

| SNP | Chr | Position | A1 | A2 | A1 freq | β | SE | P | Nearest gene | Distance |
|---|---|---|---|---|---|---|---|---|---|---|
| rs9360217 | 6 | 67338593 | G | T | 0.22 | −0.2613 | 0.0525 | 6.55E−07 | EYS | 921475 |
| rs9345875 | 6 | 67370087 | G | T | 0.21 | −0.2602 | 0.0524 | 6.95E−07 | EYS | 952969 |
| rs9342570 | 6 | 67368858 | A | T | 0.21 | −0.2589 | 0.0523 | 7.53E−07 | EYS | 951740 |
| rs9345867 | 6 | 67359694 | C | T | 0.21 | −0.258 | 0.0522 | 7.83E−07 | EYS | 942576 |
| rs2045196 | 6 | 67339443 | G | C | 0.21 | −0.265 | 0.0537 | 8.15E−07 | EYS | 922325 |
| rs1026388 | 6 | 67348220 | A | C | 0.21 | −0.2576 | 0.0523 | 8.55E−07 | EYS | 931102 |
| rs4142573 | 6 | 67388037 | T | C | 0.21 | −0.2561 | 0.052 | 8.57E−07 | EYS | 970919 |
| rs9363624 | 6 | 67387453 | C | T | 0.21 | −0.2561 | 0.052 | 8.57E−07 | EYS | 970335 |
| rs9354462 | 6 | 67383719 | T | C | 0.21 | −0.2565 | 0.0521 | 8.64E−07 | EYS | 966601 |
| rs9351587 | 6 | 67400119 | T | C | 0.21 | −0.256 | 0.052 | 8.65E−07 | EYS | 983001 |
| rs4710324 | 6 | 67352212 | T | C | 0.21 | −0.2574 | 0.0523 | 8.72E−07 | EYS | 935094 |
| rs9342572 | 6 | 67386966 | T | C | 0.21 | −0.2574 | 0.0523 | 8.72E−07 | EYS | 969848 |
| rs4710621 | 6 | 67389232 | G | A | 0.21 | −0.2559 | 0.052 | 8.74E−07 | EYS | 972114 |

TABLE 3-continued

Summary statistics for single nucleotide polymorphisms (SNPs) with P < 5.0 × 10⁻⁵
in European-American (EA) methadone dose genome-wide association studies (GWASs)

| SNP | Chr | Position | A1 | A2 | A1 freq | β | SE | P | Nearest gene | Distance |
|---|---|---|---|---|---|---|---|---|---|---|
| rs2124198 | 6 | 67366749 | C | T | 0.21 | −0.2567 | 0.0522 | 8.89E-07 | EYS | 949631 |
| rs9345880 | 6 | 67391212 | C | T | 0.21 | −0.2546 | 0.052 | 9.00E-07 | EYS | 974094 |
| rs9360224 | 6 | 67397651 | T | C | 0.21 | −0.2553 | 0.052 | 9.26E-07 | EYS | 980533 |
| rs2124199 | 6 | 67391889 | A | T | 0.21 | −0.2539 | 0.0518 | 9.65E-07 | EYS | 974771 |
| rs9354463 | 6 | 67398429 | C | T | 0.21 | −0.253 | 0.0518 | 1.05E-06 | EYS | 981311 |
| rs9345879 | 6 | 67384025 | C | T | 0.22 | −0.2532 | 0.0519 | 1.08E-06 | EYS | 966907 |
| rs9342566 | 6 | 67341860 | A | G | 0.21 | −0.2608 | 0.0536 | 1.16E-06 | EYS | 924742 |
| rs1349981 | 6 | 67360369 | A | G | 0.21 | −0.2537 | 0.0523 | 1.25E-06 | EYS | 943251 |
| rs2085201 | 6 | 67364675 | T | C | 0.21 | −0.2533 | 0.0523 | 1.30E-06 | EYS | 947557 |
| rs182987397 | 6 | 67343358 | A | C | 0.21 | −0.2622 | 0.0542 | 1.33E-06 | EYS | 926240 |
| rs187087887 | 6 | 67343359 | T | A | 0.21 | −0.2621 | 0.0542 | 1.35E-06 | EYS | 926241 |
| rs145629202 | 1 | 98766654 | G | A | 0.06 | −0.436 | 0.0915 | 1.87E-06 | SNX7 | 360582 |
| rs148501068 | 6 | 67380781 | C | T | 0.21 | −0.2523 | 0.0529 | 1.88E-06 | EYS | 963663 |
| rs2802887 | 1 | 55793434 | A | G | 0.08 | −0.3963 | 0.0832 | 1.88E-06 | USP24 | 112395 |
| rs112655778 | 1 | 98752181 | A | G | 0.06 | −0.4224 | 0.0898 | 2.52E-06 | DPYD | 365566 |
| rs58376190 | 8 | 128464949 | A | G | 0.21 | 0.2639 | 0.0563 | 2.81E-06 | POU5F1B | 35508 |
| rs12644077 | 4 | 92412577 | G | A | 0.29 | −0.2268 | 0.0484 | 2.83E-06 | CCSER1 | intronic |
| rs6455120 | 6 | 67341229 | T | C | 0.21 | −0.2469 | 0.053 | 3.23E-06 | EYS | 924111 |
| rs9643221 | 8 | 128465487 | A | G | 0.21 | 0.2616 | 0.0562 | 3.29E-06 | POU5F1B | 36046 |
| rs4683142 | 3 | 45852376 | G | C | 0.16 | −0.2773 | 0.0597 | 3.45E-06 | LZTFL1 | 12434 |
| rs1922234 | 4 | 92368033 | T | A | 0.18 | −0.2726 | 0.0587 | 3.47E-06 | CCSER1 | intronic |
| rs59573937 | 8 | 128465040 | T | C | 0.21 | 0.2608 | 0.0562 | 3.52E-06 | POU5F1B | 35599 |
| rs2352514 | 6 | 67365159 | T | C | 0.21 | −0.2476 | 0.0536 | 3.90E-06 | EYS | 948041 |
| rs6584756 | 10 | 108369238 | T | C | 0.09 | 0.3594 | 0.0779 | 4.01E-06 | SORCS1 | intronic |
| rs6532312 | 4 | 92413131 | G | A | 0.30 | −0.2226 | 0.0484 | 4.30E-06 | CCSER1 | intronic |
| rs4563143 | 19 | 29267222 | T | A | 0.23 | 0.2465 | 0.0545 | 6.18E-06 | UQCRFS1 | 430945 |
| rs6838229 | 4 | 92420171 | A | G | 0.29 | −0.2188 | 0.0484 | 6.25E-06 | CCSER1 | intronic |
| rs59139973 | 1 | 55793150 | A | G | 0.08 | −0.38 | 0.0842 | 6.31E-06 | USP24 | 112111 |
| rs4438643 | 3 | 186162919 | G | C | 0.49 | 0.2085 | 0.0465 | 7.42E-06 | DGKG | 82896 |
| rs4541401 | 3 | 186162963 | G | A | 0.49 | 0.2085 | 0.0465 | 7.42E-06 | DGKG | 82940 |
| rs6838823 | 4 | 92370384 | T | C | 0.21 | −0.2403 | 0.0538 | 8.05E-06 | CCSER1 | intronic |
| rs9643223 | 8 | 128467164 | A | G | 0.20 | 0.2543 | 0.057 | 8.25E-06 | POU5F1B | 37723 |
| rs55853356 | 3 | 186160100 | C | T | 0.49 | 0.2082 | 0.0467 | 8.37E-06 | DGKG | 80077 |
| rs55906638 | 3 | 186160457 | A | G | 0.49 | 0.2081 | 0.0468 | 8.83E-06 | DGKG | 80434 |
| rs722611 | 7 | 29514059 | C | A | 0.21 | 0.2486 | 0.056 | 9.14E-06 | CHN2 | intronic |
| rs7611186 | 3 | 186151714 | A | G | 0.46 | 0.2111 | 0.0476 | 9.33E-06 | DGKG | 71691 |
| rs11919115 | 3 | 186160910 | A | G | 0.49 | 0.207 | 0.0467 | 9.43E-06 | DGKG | 80887 |
| rs6782743 | 3 | 186159130 | A | T | 0.48 | 0.2074 | 0.0468 | 9.47E-06 | DGKG | 79107 |
| rs55928633 | 3 | 186161361 | C | A | 0.49 | 0.2069 | 0.0467 | 9.52E-06 | DGKG | 81338 |
| rs113356070 | 1 | 98755726 | A | G | 0.07 | −0.3858 | 0.0872 | 9.57E-06 | DPYD | 369111 |
| rs11578695 | 1 | 98760870 | C | A | 0.07 | −0.3857 | 0.0872 | 9.62E-06 | SNX7 | 366366 |
| rs75240562 | 1 | 98765489 | G | T | 0.07 | −0.3856 | 0.0872 | 9.67E-06 | SNX7 | 361747 |
| rs79212040 | 1 | 98746376 | G | A | 0.07 | −0.3854 | 0.0872 | 9.77E-06 | DPYD | 359761 |
| rs150249467 | 1 | 98751990 | G | C | 0.07 | −0.3853 | 0.0872 | 9.83E-06 | DPYD | 365375 |
| rs78673640 | 1 | 98736392 | T | A | 0.07 | −0.3856 | 0.0874 | 1.01E-05 | DPYD | 349777 |
| rs9351588 | 6 | 67405080 | G | T | 0.21 | −0.2322 | 0.0527 | 1.07E-05 | EYS | 987962 |
| rs6134754 | 20 | 13027457 | T | G | 0.30 | −0.2115 | 0.0481 | 1.11E-05 | SPTLC3 | intronic |
| rs10981144 | 9 | 114650176 | A | T | 0.26 | −0.2268 | 0.0516 | 1.12E-05 | UGCG | 8870 |
| rs9307096 | 4 | 92411848 | C | G | 0.22 | −0.2324 | 0.0529 | 1.13E-05 | CCSER1 | intronic |
| rs10856887 | 4 | 92366871 | A | G | 0.21 | −0.2374 | 0.0541 | 1.16E-05 | CCSER1 | intronic |
| rs6131425 | 20 | 13028905 | G | C | 0.30 | −0.2115 | 0.0482 | 1.16E-05 | SPTLC3 | intronic |
| rs1922231 | 4 | 92368444 | C | T | 0.21 | −0.2339 | 0.0535 | 1.25E-05 | CCSER1 | intronic |
| rs6787529 | 3 | 186164346 | C | G | 0.49 | 0.2037 | 0.0466 | 1.25E-05 | DGKG | 84323 |
| rs11916012 | 3 | 186158483 | A | G | 0.48 | 0.2049 | 0.0469 | 1.26E-05 | DGKG | 78460 |
| rs1835661 | 20 | 13025560 | T | C | 0.30 | −0.2099 | 0.0483 | 1.41E-05 | SPTLC3 | intronic |
| rs4805263 | 19 | 29217637 | G | A | 0.22 | 0.2355 | 0.0542 | 1.41E-05 | UQCRFS1 | 480530 |
| rs10025122 | 4 | 92379698 | T | C | 0.21 | −0.2335 | 0.0538 | 1.44E-05 | CCSER1 | intronic |
| rs199065 | 6 | 23484583 | T | C | 0.39 | 0.2059 | 0.0475 | 1.48E-05 | NRSN1 | 641831 |
| rs268594 | 8 | 71513130 | T | C | 0.26 | −0.2202 | 0.0509 | 1.54E-05 | TRAM1 | intronic |
| rs12763487 | 10 | 12490818 | G | A | 0.19 | −0.2547 | 0.059 | 1.60E-05 | CAMK1D | intronic |
| rs268601 | 8 | 71518548 | C | T | 0.26 | −0.2192 | 0.0508 | 1.62E-05 | TRAM1 | intronic |
| rs268596 | 8 | 71514303 | A | G | 0.26 | −0.2196 | 0.0509 | 1.62E-05 | TRAM1 | intronic |
| rs12649871 | 4 | 92381080 | T | C | 0.21 | −0.2316 | 0.0537 | 1.63E-05 | CCSER1 | intronic |
| rs13295839 | 9 | 114639407 | G | T | 0.26 | −0.2234 | 0.0518 | 1.63E-05 | UGCG | 19639 |
| rs2742362 | 3 | 45875149 | T | G | 0.17 | −0.2492 | 0.0578 | 1.64E-05 | LZTFL1 | intronic |
| rs7619982 | 3 | 186151172 | C | T | 0.48 | 0.2012 | 0.0467 | 1.66E-05 | DGKG | 71149 |
| rs12301000 | 12 | 76665015 | T | A | 0.29 | 0.2283 | 0.053 | 1.67E-05 | BBS10 | 73251 |
| rs2204873 | 4 | 92367596 | T | C | 0.21 | −0.2316 | 0.0538 | 1.69E-05 | CCSER1 | intronic |
| rs268592 | 8 | 71512349 | A | T | 0.27 | −0.2187 | 0.0509 | 1.75E-05 | TRAM1 | intronic |
| rs7828855 | 8 | 128466988 | A | T | 0.19 | 0.247 | 0.0575 | 1.76E-05 | POU5F1B | 37547 |
| rs4964107 | 12 | 64915332 | A | G | 0.09 | −0.3372 | 0.0785 | 1.76E-05 | TBK1 | 19433 |
| rs7841264 | 8 | 128466814 | T | C | 0.19 | 0.2435 | 0.0567 | 1.77E-05 | POU5F1B | 37373 |
| rs2056986 | 6 | 23466015 | A | C | 0.28 | 0.2194 | 0.0511 | 1.78E-05 | NRSN1 | 660399 |
| rs268584 | 8 | 71468669 | G | A | 0.26 | −0.2211 | 0.0515 | 1.78E-05 | TRAM1 | 16784 |

TABLE 3-continued

Summary statistics for single nucleotide polymorphisms (SNPs) with P < 5.0 × 10⁻⁵
in European-American (EA) methadone dose genome-wide association studies (GWASs)

| SNP | Chr | Position | A1 | A2 | A1 freq | β | SE | P | Nearest gene | Distance |
|---|---|---|---|---|---|---|---|---|---|---|
| rs1997498 | 4 | 92422781 | A | C | 0.27 | −0.2135 | 0.0498 | 1.83E−05 | CCSER1 | intronic |
| rs9843446 | 3 | 45893243 | C | G | 0.17 | −0.2478 | 0.0578 | 1.83E−05 | LZTFL1 | intronic |
| rs1922235 | 4 | 92367917 | G | A | 0.21 | −0.2306 | 0.0538 | 1.84E−05 | CCSER1 | intronic |
| rs17151691 | 10 | 12482777 | C | A | 0.19 | −0.2476 | 0.0578 | 1.86E−05 | CAMK1D | intronic |
| rs4936290 | 11 | 114009255 | C | A | 0.32 | −0.2054 | 0.048 | 1.90E−05 | ZBTB16 | intronic |
| rs268628 | 8 | 71560505 | T | C | 0.26 | −0.2182 | 0.051 | 1.90E−05 | LACTB2 | intronic |
| rs7622585 | 3 | 186151558 | C | T | 0.48 | 0.2001 | 0.0468 | 1.93E−05 | DGKG | 71535 |
| rs7632934 | 3 | 186151667 | G | A | 0.48 | 0.2001 | 0.0468 | 1.93E−05 | DGKG | 71644 |
| rs10981115 | 9 | 114608646 | T | C | 0.18 | −0.2466 | 0.0577 | 1.94E−05 | UGCG | 50400 |
| rs1922233 | 4 | 92368346 | G | A | 0.21 | −0.2295 | 0.0537 | 1.95E−05 | CCSER1 | intronic |
| rs7611289 | 3 | 186151797 | A | G | 0.48 | 0.2 | 0.0468 | 1.95E−05 | DGKG | 71774 |
| rs10981114 | 9 | 114607370 | C | T | 0.18 | −0.2465 | 0.0577 | 1.96E−05 | UGCG | 51676 |
| rs10007400 | 4 | 92369162 | T | A | 0.21 | −0.2293 | 0.0537 | 1.98E−05 | CCSER1 | intronic |
| rs2742361 | 3 | 45870645 | G | A | 0.17 | −0.2468 | 0.0578 | 1.98E−05 | LZTFL1 | intronic |
| rs10981146 | 9 | 114657260 | C | T | 0.26 | −0.2216 | 0.0519 | 1.98E−05 | UGCG | 1786 |
| rs7164778 | 15 | 80884837 | G | A | 0.27 | 0.2181 | 0.0511 | 1.99E−05 | ARNT2 | intronic |
| rs61378972 | 19 | 29218742 | T | C | 0.22 | 0.2343 | 0.055 | 2.07E−05 | UQCRFS1 | 479425 |
| rs7046046 | 9 | 114617115 | T | C | 0.18 | −0.2458 | 0.0577 | 2.07E−05 | UGCG | 41931 |
| rs11946031 | 4 | 92421742 | T | A | 0.27 | −0.2117 | 0.0497 | 2.07E−05 | CCSER1 | intronic |
| rs7046120 | 9 | 114617030 | T | G | 0.18 | −0.25 | 0.0587 | 2.08E−05 | UGCG | 42016 |
| rs11731642 | 4 | 92421296 | G | A | 0.27 | −0.2116 | 0.0497 | 2.09E−05 | CCSER1 | intronic |
| rs2673059 | 3 | 45844295 | C | T | 0.18 | −0.248 | 0.0583 | 2.13E−05 | SLC6A20 | 6260 |
| rs7042346 | 9 | 114661611 | G | T | 0.26 | −0.2181 | 0.0514 | 2.23E−05 | UGCG | intronic |
| rs114738466 | 7 | 18189185 | A | T | 0.07 | 0.3824 | 0.0903 | 2.27E−05 | HDAC9 | intronic |
| rs11734211 | 4 | 92414976 | T | A | 0.30 | −0.2118 | 0.05 | 2.30E−05 | CCSER1 | intronic |
| rs7874031 | 9 | 114625609 | C | T | 0.18 | −0.2444 | 0.0577 | 2.30E−05 | UGCG | 33437 |
| rs268627 | 8 | 71561041 | C | T | 0.26 | −0.2163 | 0.0511 | 2.33E−05 | LACTB2 | intronic |
| rs28685630 | 4 | 92371156 | T | A | 0.21 | −0.2271 | 0.0537 | 2.37E−05 | CCSER1 | intronic |
| rs4878040 | 9 | 89673047 | T | C | 0.08 | −0.3603 | 0.0853 | 2.38E−05 | C9orf170 | 90512 |
| rs4459508 | 15 | 80887506 | T | C | 0.26 | 0.2152 | 0.0509 | 2.39E−05 | ARNT2 | UTR3 |
| rs6852821 | 4 | 92422256 | G | A | 0.44 | −0.1847 | 0.0437 | 2.40E−05 | CCSER1 | intronic |
| rs9642878 | 8 | 128465268 | A | G | 0.18 | 0.248 | 0.0587 | 2.42E−05 | POU5F1B | 35827 |
| rs12379191 | 9 | 114594188 | A | G | 0.18 | −0.2445 | 0.0579 | 2.44E−05 | C9orf84 | 48409 |
| rs12348354 | 9 | 114661266 | G | T | 0.26 | −0.2169 | 0.0514 | 2.47E−05 | UGCG | intronic |
| rs4683144 | 3 | 45864256 | T | C | 0.18 | −0.2433 | 0.0577 | 2.51E−05 | LZTFL1 | 1188 |
| rs12380778 | 9 | 19133582 | T | G | 0.08 | −0.3681 | 0.0874 | 2.51E−05 | PLIN2 | 5978 |
| rs1997497 | 4 | 92365182 | C | T | 0.21 | −0.2239 | 0.0531 | 2.51E−05 | CCSER1 | intronic |
| rs7172548 | 15 | 80886513 | T | C | 0.28 | 0.2143 | 0.0509 | 2.58E−05 | ARNT2 | UTR3 |
| rs11730700 | 4 | 92420956 | G | T | 0.44 | −0.1838 | 0.0437 | 2.63E−05 | CCSER1 | intronic |
| rs117442062 | 19 | 29256823 | T | A | 0.19 | 0.2516 | 0.06 | 2.78E−05 | UQCRFS1 | 441344 |
| rs117946634 | 19 | 29256822 | T | G | 0.19 | 0.2516 | 0.06 | 2.78E−05 | UQCRFS1 | 441345 |
| rs34218744 | 19 | 29256821 | T | A | 0.19 | 0.2516 | 0.06 | 2.78E−05 | UQCRFS1 | 441346 |
| rs10504478 | 8 | 71544918 | C | T | 0.19 | −0.2363 | 0.0564 | 2.82E−05 | LACTB2 | 4583 |
| rs56067816 | 19 | 29218354 | A | C | 0.22 | 0.2295 | 0.0548 | 2.85E−05 | UQCRFS1 | 479813 |
| rs4979061 | 9 | 114657719 | T | C | 0.26 | −0.2156 | 0.0515 | 2.87E−05 | UGCG | 1327 |
| rs12800436 | 11 | 116558802 | T | G | 0.18 | −0.2494 | 0.0596 | 2.89E−05 | BUD13 | 60084 |
| rs9971436 | 11 | 87947490 | A | G | 0.08 | −0.3582 | 0.0857 | 2.89E−05 | RAB38 | 38855 |
| rs10777060 | 12 | 76632508 | C | T | 0.31 | 0.2133 | 0.051 | 2.92E−05 | BBS10 | 105758 |
| rs4964089 | 12 | 64931049 | C | G | 0.09 | −0.3181 | 0.0761 | 2.95E−05 | TBK1 | 35150 |
| rs7781003 | 7 | 29516650 | T | G | 0.33 | 0.1964 | 0.047 | 2.96E−05 | CHN2 | intronic |
| rs13272623 | 8 | 71544748 | G | T | 0.19 | −0.2356 | 0.0564 | 2.98E−05 | LACTB2 | 4753 |
| rs12498268 | 4 | 92405232 | A | G | 0.22 | −0.2263 | 0.0542 | 3.01E−05 | CCSER1 | intronic |
| rs7172912 | 15 | 80886555 | A | G | 0.27 | 0.2125 | 0.0509 | 3.02E−05 | ARNT2 | UTR3 |
| rs6532311 | 4 | 92407620 | T | A | 0.21 | −0.2258 | 0.0541 | 3.03E−05 | CCSER1 | intronic |
| rs151154219 | 4 | 153663135 | A | G | 0.44 | 0.2105 | 0.0505 | 3.10E−05 | TIGD4 | 27371 |
| rs268589 | 8 | 71464671 | C | T | 0.26 | −0.2162 | 0.0519 | 3.14E−05 | TRAM1 | 20782 |
| rs10981147 | 9 | 114658807 | T | C | 0.26 | −0.2145 | 0.0515 | 3.15E−05 | UGCG | 397 |
| rs10125601 | 9 | 114628073 | A | G | 0.18 | −0.2385 | 0.0573 | 3.19E−05 | UGCG | 30973 |
| rs35571096 | 8 | 71550144 | G | A | 0.19 | −0.2347 | 0.0564 | 3.20E−05 | LACTB2 | intronic |
| rs9918763 | 8 | 71549007 | T | C | 0.19 | −0.2347 | 0.0564 | 3.20E−05 | LACTB2 | 494 |
| rs10406794 | 19 | 29228056 | A | G | 0.22 | 0.2251 | 0.0541 | 3.21E−05 | UQCRFS1 | 470111 |
| rs6804422 | 3 | 186162183 | C | A | 0.47 | 0.1971 | 0.0474 | 3.24E−05 | DGKG | 82160 |
| rs13262215 | 8 | 71544091 | A | G | 0.20 | −0.2349 | 0.0565 | 3.25E−05 | LACTB2 | 5410 |
| rs10817235 | 9 | 114658273 | C | T | 0.26 | −0.2141 | 0.0515 | 3.26E−05 | UGCG | 931 |
| rs141302559 | 4 | 92388635 | T | A | 0.22 | −0.2285 | 0.055 | 3.30E−05 | CCSER1 | intronic |
| rs10101764 | 8 | 71542579 | C | T | 0.19 | −0.2339 | 0.0563 | 3.30E−05 | LACTB2 | 6922 |
| rs2827033 | 21 | 23158504 | G | A | 0.38 | 0.2073 | 0.0499 | 3.30E−05 | NCAM2 | 245987 |
| rs10981131 | 9 | 114635278 | C | T | 0.18 | −0.2413 | 0.0581 | 3.32E−05 | UGCG | 23768 |
| rs35557557 | 8 | 71543628 | G | A | 0.19 | −0.2338 | 0.0563 | 3.32E−05 | LACTB2 | 5873 |
| rs271629 | 19 | 18623198 | A | G | 0.35 | 0.1918 | 0.0462 | 3.34E−05 | ELL | intronic |
| rs13262040 | 8 | 71544207 | T | C | 0.19 | −0.2337 | 0.0563 | 3.35E−05 | LACTB2 | 5294 |
| rs17819170 | 22 | 20767791 | T | C | 0.22 | −0.2395 | 0.0577 | 3.35E−05 | ZNF74 | 5038 |
| rs11740642 | 5 | 162473567 | A | G | 0.07 | −0.3748 | 0.0904 | 3.35E−05 | CCNG1 | 391010 |
| rs113602622 | 1 | 98771485 | G | C | 0.07 | −0.346 | 0.0835 | 3.38E−05 | SNX7 | 355751 |

TABLE 3-continued

Summary statistics for single nucleotide polymorphisms (SNPs) with P < 5.0 × 10⁻⁵ in European-American (EA) methadone dose genome-wide association studies (GWASs)

| SNP | Chr | Position | A1 | A2 | A1 freq | β | SE | P | Nearest gene | Distance |
|---|---|---|---|---|---|---|---|---|---|---|
| rs77565080 | 1 | 98772710 | C | T | 0.07 | −0.346 | 0.0835 | 3.38E−05 | SNX7 | 354526 |
| rs77970352 | 1 | 98768653 | C | T | 0.07 | −0.346 | 0.0835 | 3.38E−05 | SNX7 | 358583 |
| rs78173095 | 1 | 98771478 | G | C | 0.07 | −0.346 | 0.0835 | 3.38E−05 | SNX7 | 355758 |
| rs74930117 | 1 | 98784461 | T | C | 0.07 | −0.3463 | 0.0836 | 3.40E−05 | SNX7 | 342775 |
| rs6495511 | 15 | 80888783 | G | A | 0.28 | 0.2098 | 0.0506 | 3.42E−05 | ARNT2 | UTR3 |
| rs2191032 | 3 | 45906572 | C | T | 0.17 | −0.2354 | 0.0568 | 3.45E−05 | LZTFL1 | intronic |
| rs111520245 | 1 | 98774560 | C | G | 0.07 | −0.3456 | 0.0835 | 3.45E−05 | SNX7 | 352676 |
| rs111541644 | 1 | 98776154 | A | G | 0.07 | −0.3456 | 0.0835 | 3.45E−05 | SNX7 | 351082 |
| rs17136824 | 10 | 12464495 | A | G | 0.17 | −0.2506 | 0.0605 | 3.48E−05 | CAMK1D | intronic |
| rs76677766 | 1 | 98775508 | T | C | 0.07 | −0.3453 | 0.0835 | 3.51E−05 | SNX7 | 351728 |
| rs6532305 | 4 | 92353722 | A | G | 0.17 | −0.2455 | 0.0593 | 3.51E−05 | CCSER1 | intronic |
| rs16961809 | 19 | 29226299 | T | C | 0.22 | 0.2252 | 0.0544 | 3.52E−05 | UQCRFS1 | 471868 |
| rs13274576 | 8 | 71532678 | C | G | 0.19 | −0.233 | 0.0563 | 3.53E−05 | TRAM1 | 11984 |
| rs28550678 | 8 | 71535043 | G | A | 0.19 | −0.233 | 0.0563 | 3.53E−05 | TRAM1 | 14349 |
| rs28712644 | 8 | 71534710 | G | A | 0.19 | −0.233 | 0.0563 | 3.53E−05 | TRAM1 | 14016 |
| rs12316944 | 12 | 64926748 | T | G | 0.09 | −0.3157 | 0.0763 | 3.55E−05 | TBK1 | 30849 |
| rs13280965 | 8 | 71538686 | T | C | 0.19 | −0.2329 | 0.0563 | 3.56E−05 | LACTB2 | 10815 |
| rs4964110 | 12 | 64930823 | T | C | 0.09 | −0.3152 | 0.0762 | 3.57E−05 | TBK1 | 34924 |
| rs4964112 | 12 | 64932775 | A | G | 0.09 | −0.3152 | 0.0762 | 3.57E−05 | TBK1 | 36876 |
| rs68094298 | 12 | 64929040 | C | G | 0.09 | −0.3152 | 0.0762 | 3.57E−05 | TBK1 | 33141 |
| rs142765797 | 8 | 71541334 | T | G | 0.19 | −0.2328 | 0.0563 | 3.59E−05 | LACTB2 | 8167 |
| rs145863039 | 8 | 71541503 | C | G | 0.19 | −0.2328 | 0.0563 | 3.59E−05 | LACTB2 | 7998 |
| rs151063730 | 8 | 71541336 | T | A | 0.19 | −0.2328 | 0.0563 | 3.59E−05 | LACTB2 | 8165 |
| rs271622 | 19 | 18629277 | G | A | 0.35 | 0.191 | 0.0462 | 3.60E−05 | ELL | intronic |
| rs10087148 | 8 | 71542743 | T | G | 0.19 | −0.2327 | 0.0563 | 3.62E−05 | LACTB2 | 6758 |
| rs10878187 | 12 | 64935746 | T | C | 0.09 | −0.3149 | 0.0762 | 3.63E−05 | TBK1 | 39847 |
| rs1922236 | 4 | 92366373 | C | G | 0.21 | −0.2215 | 0.0536 | 3.63E−05 | CCSER1 | intronic |
| rs76793464 | 17 | 55506670 | A | G | 0.07 | −0.3764 | 0.0912 | 3.64E−05 | MSI2 | intronic |
| rs7968623 | 12 | 64934166 | C | G | 0.09 | −0.3148 | 0.0762 | 3.65E−05 | TBK1 | 38267 |
| rs271621 | 19 | 18631332 | A | C | 0.35 | 0.1912 | 0.0463 | 3.67E−05 | ELL | intronic |
| rs7579961 | 2 | 227776976 | A | T | 0.38 | 0.1854 | 0.0449 | 3.68E−05 | RHBDD1 | intronic |
| rs7592387 | 2 | 227777095 | G | A | 0.38 | 0.1854 | 0.0449 | 3.68E−05 | RHBDD1 | intronic |
| rs10099486 | 8 | 71538973 | T | C | 0.19 | −0.2324 | 0.0563 | 3.70E−05 | LACTB2 | 10528 |
| rs10204368 | 2 | 227774244 | C | G | 0.38 | 0.1853 | 0.0449 | 3.72E−05 | RHBDD1 | intronic |
| rs10210763 | 2 | 227776029 | T | G | 0.38 | 0.1853 | 0.0449 | 3.72E−05 | RHBDD1 | intronic |
| rs1346618 | 2 | 227771988 | C | T | 0.38 | 0.1853 | 0.0449 | 3.72E−05 | RHBDD1 | intronic |
| rs1366756 | 2 | 227772038 | A | G | 0.38 | 0.1853 | 0.0449 | 3.72E−05 | RHBDD1 | intronic |
| rs2163041 | 2 | 227772480 | C | T | 0.38 | 0.1853 | 0.0449 | 3.72E−05 | RHBDD1 | intronic |
| rs2396433 | 2 | 227772502 | G | A | 0.38 | 0.1853 | 0.0449 | 3.72E−05 | RHBDD1 | intronic |
| rs4675120 | 2 | 227774888 | T | C | 0.38 | 0.1853 | 0.0449 | 3.72E−05 | RHBDD1 | intronic |
| rs7561378 | 2 | 227772248 | C | T | 0.38 | 0.1853 | 0.0449 | 3.72E−05 | RHBDD1 | intronic |
| rs1922216 | 4 | 92366263 | A | G | 0.21 | −0.221 | 0.0536 | 3.78E−05 | CCSER1 | intronic |
| rs268599 | 8 | 71517401 | C | A | 0.26 | −0.2102 | 0.051 | 3.80E−05 | TRAM1 | intronic |
| rs6854368 | 4 | 92365952 | T | A | 0.21 | −0.2209 | 0.0536 | 3.81E−05 | CCSER1 | intronic |
| rs271623 | 19 | 18628947 | G | A | 0.35 | 0.1904 | 0.0462 | 3.81E−05 | ELL | intronic |
| rs56249352 | 12 | 64913823 | C | G | 0.09 | −0.335 | 0.0813 | 3.82E−05 | TBK1 | 17924 |
| rs55976444 | 19 | 29265214 | C | G | 0.21 | 0.2307 | 0.056 | 3.84E−05 | UQCRFS1 | 432953 |
| rs11692572 | 2 | 227774503 | G | C | 0.38 | 0.1862 | 0.0452 | 3.84E−05 | RHBDD1 | intronic |
| rs76195 | 19 | 18629830 | C | T | 0.35 | 0.1903 | 0.0462 | 3.85E−05 | ELL | intronic |
| rs12407972 | 1 | 162351454 | G | A | 0.16 | 0.2467 | 0.0599 | 3.85E−05 | C1orf226 | intronic |
| rs1997496 | 4 | 92365316 | A | G | 0.21 | −0.2206 | 0.0536 | 3.90E−05 | CCSER1 | intronic |
| rs139250294 | 3 | 130838467 | C | G | 0.07 | −0.3848 | 0.0936 | 3.91E−05 | NEK11 | intronic |
| rs268562 | 8 | 71494780 | G | T | 0.26 | −0.2103 | 0.0511 | 3.91E−05 | TRAM1 | intronic |
| rs55884228 | 19 | 29243897 | T | G | 0.21 | 0.2296 | 0.0558 | 3.92E−05 | UQCRFS1 | 454270 |
| rs76194 | 19 | 18630580 | G | T | 0.35 | 0.1905 | 0.0463 | 3.92E−05 | ELL | intronic |
| rs10167422 | 2 | 227777554 | A | G | 0.38 | 0.1851 | 0.045 | 3.94E−05 | RHBDD1 | intronic |
| rs11686072 | 2 | 227777493 | T | A | 0.38 | 0.185 | 0.045 | 3.98E−05 | RHBDD1 | intronic |
| rs12030658 | 1 | 116388611 | T | C | 0.34 | 0.1928 | 0.0469 | 3.98E−05 | NHLH2 | 4864 |
| rs10963987 | 9 | 19142014 | A | C | 0.08 | −0.3449 | 0.084 | 3.99E−05 | PLIN2 | 14410 |
| rs191619682 | 12 | 64937205 | G | C | 0.08 | −0.365 | 0.0889 | 3.99E−05 | TBK1 | 41306 |
| rs4675118 | 2 | 227773157 | A | C | 0.38 | 0.1845 | 0.0449 | 4.01E−05 | RHBDD1 | intronic |
| rs4675119 | 2 | 227774635 | C | A | 0.38 | 0.1845 | 0.0449 | 4.01E−05 | RHBDD1 | intronic |
| rs1922217 | 4 | 92357499 | A | G | 0.21 | −0.2189 | 0.0533 | 4.05E−05 | CCSER1 | intronic |
| rs1922218 | 4 | 92357436 | G | A | 0.21 | −0.2189 | 0.0533 | 4.05E−05 | CCSER1 | intronic |
| rs61847407 | 10 | 12462602 | G | A | 0.17 | −0.2497 | 0.0608 | 4.05E−05 | CAMK1D | intronic |
| rs10193316 | 2 | 227777650 | G | A | 0.38 | 0.1848 | 0.045 | 4.06E−05 | RHBDD1 | intronic |
| rs10193404 | 2 | 227777757 | G | A | 0.38 | 0.1848 | 0.045 | 4.06E−05 | RHBDD1 | intronic |
| rs7970071 | 12 | 64943222 | A | T | 0.10 | −0.3088 | 0.0752 | 4.06E−05 | TBK1 | 47323 |
| rs271626 | 19 | 18627067 | C | T | 0.35 | 0.1897 | 0.0462 | 4.07E−05 | ELL | intronic |
| rs9856760 | 3 | 45906356 | G | A | 0.18 | −0.2327 | 0.0567 | 4.10E−05 | LZTFL1 | intronic |
| rs7001369 | 8 | 71537141 | A | G | 0.19 | −0.231 | 0.0563 | 4.12E−05 | LACTB2 | 12360 |
| rs149387740 | 19 | 29248757 | A | C | 0.21 | 0.2289 | 0.0558 | 4.14E−05 | UQCRFS1 | 449410 |
| rs56293553 | 19 | 29270455 | G | A | 0.21 | 0.2289 | 0.0558 | 4.14E−05 | UQCRFS1 | 427712 |
| rs76310357 | 1 | 98784279 | C | T | 0.07 | −0.3531 | 0.0862 | 4.16E−05 | SNX7 | 342957 |

TABLE 3-continued

Summary statistics for single nucleotide polymorphisms (SNPs) with $P < 5.0 \times 10^{-5}$
in European-American (EA) methadone dose genome-wide association studies (GWASs)

| SNP | Chr | Position | A1 | A2 | A1 freq | β | SE | P | Nearest gene | Distance |
|---|---|---|---|---|---|---|---|---|---|---|
| rs73025085 | 19 | 29247018 | A | C | 0.21 | 0.2288 | 0.0558 | 4.17E−05 | UQCRFS1 | 451149 |
| rs73029049 | 19 | 29275534 | A | C | 0.21 | 0.2288 | 0.0558 | 4.17E−05 | UQCRFS1 | 422633 |
| rs17138617 | 5 | 115333425 | T | G | 0.12 | −0.2837 | 0.0692 | 4.18E−05 | LVRN | intronic |
| rs271628 | 19 | 18624333 | G | A | 0.35 | 0.1894 | 0.0462 | 4.18E−05 | ELL | intronic |
| rs73029050 | 19 | 29276554 | T | G | 0.21 | 0.2291 | 0.0559 | 4.21E−05 | UQCRFS1 | 421613 |
| rs73122393 | 12 | 64926110 | T | A | 0.09 | −0.3135 | 0.0765 | 4.21E−05 | TBK1 | 30211 |
| rs1429267 | 2 | 227767593 | C | G | 0.38 | 0.1844 | 0.045 | 4.22E−05 | RHBDD1 | intronic |
| rs16822890 | 2 | 227761477 | A | G | 0.38 | 0.1844 | 0.045 | 4.22E−05 | RHBDD1 | intronic |
| rs1835158 | 2 | 227763993 | A | C | 0.38 | 0.1844 | 0.045 | 4.22E−05 | RHBDD1 | intronic |
| rs60141402 | 2 | 227761445 | C | A | 0.38 | 0.1844 | 0.045 | 4.22E−05 | RHBDD1 | intronic |
| rs9288617 | 2 | 227762815 | C | G | 0.38 | 0.1844 | 0.045 | 4.22E−05 | RHBDD1 | intronic |
| rs72698339 | 9 | 19142215 | G | A | 0.08 | −0.3453 | 0.0844 | 4.25E−05 | PLIN2 | 14611 |
| rs4675114 | 2 | 227768362 | T | C | 0.38 | 0.1843 | 0.045 | 4.26E−05 | RHBDD1 | intronic |
| rs4675116 | 2 | 227769607 | C | A | 0.38 | 0.1843 | 0.045 | 4.26E−05 | RHBDD1 | intronic |
| rs6752707 | 2 | 227766822 | G | C | 0.38 | 0.1843 | 0.045 | 4.26E−05 | RHBDD1 | intronic |
| rs12615988 | 2 | 227769000 | A | G | 0.38 | 0.1847 | 0.0451 | 4.26E−05 | RHBDD1 | intronic |
| rs6993519 | 8 | 71540938 | G | A | 0.18 | −0.2354 | 0.0575 | 4.29E−05 | LACTB2 | 8563 |
| rs4675113 | 2 | 227766339 | A | G | 0.38 | 0.1842 | 0.045 | 4.30E−05 | RHBDD1 | intronic |
| rs4696154 | 4 | 153663112 | G | A | 0.48 | 0.2067 | 0.0505 | 4.30E−05 | TIGD4 | 27394 |
| rs66959645 | 2 | 227761582 | A | C | 0.38 | 0.1854 | 0.0453 | 4.31E−05 | RHBDD1 | intronic |
| rs34113156 | 19 | 29270822 | A | G | 0.21 | 0.2287 | 0.0559 | 4.34E−05 | UQCRFS1 | 427345 |
| rs56322221 | 19 | 29270349 | T | A | 0.21 | 0.2287 | 0.0559 | 4.34E−05 | UQCRFS1 | 427818 |
| rs6771524 | 3 | 25037250 | G | A | 0.23 | −0.2254 | 0.0551 | 4.35E−05 | RARB | 178573 |
| rs12449590 | 17 | 71347027 | A | G | 0.40 | 0.1906 | 0.0466 | 4.36E−05 | SDK2 | intronic |
| rs6774166 | 3 | 25043523 | G | A | 0.24 | −0.2237 | 0.0547 | 4.37E−05 | RARB | 172300 |
| rs73029042 | 19 | 29267979 | T | A | 0.21 | 0.2286 | 0.0559 | 4.37E−05 | UQCRFS1 | 430188 |
| rs978909 | 2 | 227771389 | G | T | 0.38 | 0.184 | 0.045 | 4.38E−05 | RHBDD1 | intronic |
| rs72657626 | 6 | 23491337 | T | C | 0.28 | 0.2105 | 0.0515 | 4.41E−05 | NRSN1 | 635077 |
| rs79015053 | 2 | 229377652 | T | C | 0.11 | 0.3024 | 0.074 | 4.43E−05 | SPHKAP | 331291 |
| rs112383987 | 19 | 29261081 | T | C | 0.21 | 0.2284 | 0.0559 | 4.44E−05 | UQCRFS1 | 437086 |
| rs113665848 | 19 | 29260971 | T | C | 0.21 | 0.2284 | 0.0559 | 4.44E−05 | UQCRFS1 | 437196 |
| rs73029014 | 19 | 29257655 | C | G | 0.21 | 0.2283 | 0.0559 | 4.47E−05 | UQCRFS1 | 440512 |
| rs720501 | 2 | 227778445 | T | C | 0.38 | 0.1841 | 0.0451 | 4.51E−05 | RHBDD1 | intronic |
| rs11774577 | 8 | 21228629 | C | G | 0.38 | 0.1902 | 0.0466 | 4.52E−05 | GFRA2 | 320901 |
| rs3731593 | 2 | 227773924 | G | A | 0.38 | 0.184 | 0.0451 | 4.56E−05 | RHBDD1 | intronic |
| rs17136827 | 10 | 12464973 | C | T | 0.17 | −0.2464 | 0.0604 | 4.56E−05 | CAMK1D | intronic |
| rs13123986 | 4 | 92382683 | C | G | 0.36 | −0.1852 | 0.0454 | 4.57E−05 | CCSER1 | intronic |
| rs7484 | 15 | 80890101 | C | T | 0.28 | 0.2064 | 0.0506 | 4.57E−05 | ARNT2 | UTR3 |
| rs55788919 | 19 | 29260780 | C | T | 0.21 | 0.228 | 0.0559 | 4.58E−05 | UQCRFS1 | 437387 |
| rs8109573 | 19 | 18617151 | T | G | 0.35 | 0.188 | 0.0461 | 4.59E−05 | ELL | intronic |
| rs10197757 | 2 | 227763244 | G | T | 0.38 | 0.1835 | 0.045 | 4.60E−05 | RHBDD1 | intronic |
| rs17138628 | 7 | 18166751 | G | A | 0.07 | 0.347 | 0.0852 | 4.60E−05 | HDAC9 | intronic |
| rs34746918 | 19 | 18539744 | T | C | 0.34 | 0.1924 | 0.0472 | 4.63E−05 | SSBP4 | intronic |
| rs7242411 | 18 | 39445807 | A | G | 0.06 | −0.4039 | 0.0992 | 4.64E−05 | PIK3C3 | 89356 |
| rs3935130 | 15 | 80884171 | A | C | 0.27 | 0.2106 | 0.0517 | 4.68E−05 | ARNT2 | intronic |
| rs6495512 | 15 | 80891753 | A | G | 0.28 | 0.2065 | 0.0507 | 4.69E−05 | ARNT2 | 1476 |
| rs8106096 | 19 | 18536416 | G | C | 0.33 | 0.195 | 0.0479 | 4.73E−05 | SSBP4 | intronic |
| rs62296729 | 4 | 19491007 | A | G | 0.12 | 0.2719 | 0.0668 | 4.74E−05 | SLIT2 | 762521 |
| rs28579010 | 21 | 44110306 | C | T | 0.39 | −0.19 | 0.0467 | 4.78E−05 | PDE9A | intronic |
| rs4632613 | 4 | 92385067 | T | C | 0.21 | −0.2175 | 0.0535 | 4.85E−05 | CCSER1 | intronic |
| rs4808136 | 19 | 18618867 | A | G | 0.35 | 0.1878 | 0.0462 | 4.86E−05 | ELL | intronic |
| rs8107347 | 19 | 18612748 | A | G | 0.35 | 0.1877 | 0.0462 | 4.90E−05 | ELL | intronic |
| rs8107351 | 19 | 18612758 | A | G | 0.35 | 0.1877 | 0.0462 | 4.90E−05 | ELL | intronic |
| rs1420128 | 7 | 29512502 | G | A | 0.33 | 0.1929 | 0.0475 | 4.94E−05 | CHN2 | intronic |
| rs79240360 | 2 | 229375847 | C | T | 0.11 | 0.3005 | 0.074 | 4.94E−05 | SPHKAP | 329486 |
| rs1033222 | 3 | 130957740 | G | T | 0.12 | −0.2765 | 0.0681 | 4.96E−05 | NEK11 | intronic |
| rs34736326 | 10 | 10065028 | G | T | 0.44 | −0.1802 | 0.0444 | 4.99E−05 | CELF2 | 982231 |
| rs1155976 | 2 | 229376699 | A | G | 0.11 | 0.2999 | 0.0739 | 5.00E−05 | SPHKAP | 330338 |

For each SNP, separate columns provide the chromosome (Chr), position (genome build hg19), minor (A1) allele, major (A2) allele, minor (A1) allele frequency, β, standard error (SE), P value, the nearest RefSeq11 protein coding gene as determined by the ANNOVAR12 software package, and distance from the nearest gene. The sign of β reflects the direction of effect of the minor (A1) allele.

TABLE 4

Candidate functional alleles in previously studied metabolizing enzymes

| Gene | RSID | Cytochrome P450 Nomenclature | Annotation | β | SE | P |
|---|---|---|---|---|---|---|
| | | | | AA | | |
| CYP3A4 | rs2740574 | CYP3A4*1B | Promoter[21] | −0.050 | 0.083 | 0.55 |
| CYP2B6 | rs3745274 | CYP2B6*9 | Missense[60,80] | −0.0089 | 0.074 | 0.91 |
| CYP2D6 | rs3892097 | CYP2D6*4 | Splice site[60] | −0.17 | 0.14 | 0.23 |
| | | | | EA | | |
| CYP3A4 | rs2740574 | CYP3A4*1B | Promoter[21] | −0.0047 | 0.11 | 0.97 |
| CYP2B6 | rs3745274 | CYP2B6*9 | Missense[60,80] | −0.028 | 0.052 | 0.59 |
| CYP2D6 | rs3892097 | CYP2D6*4 | Splice site[60] | −0.16 | 0.057 | $5.4 \times 10^{-3}$ |
| | | | | AA and EA Meta | | |
| CYP3A4 | rs2740574 | CYP3A4*1B | Promoter[21] | −0.034 | 0.067 | 0.61 |
| CYP2B6 | rs3745274 | CYP2B6*9 | Missense[60,80] | −0.022 | 0.043 | 0.61 |
| CYP2D6 | rs3892097 | CYP2D6*4 | Splice site[60] | −0.16 | 0.053 | $2.4 \times 10^{-3}$ |

Figure 3:
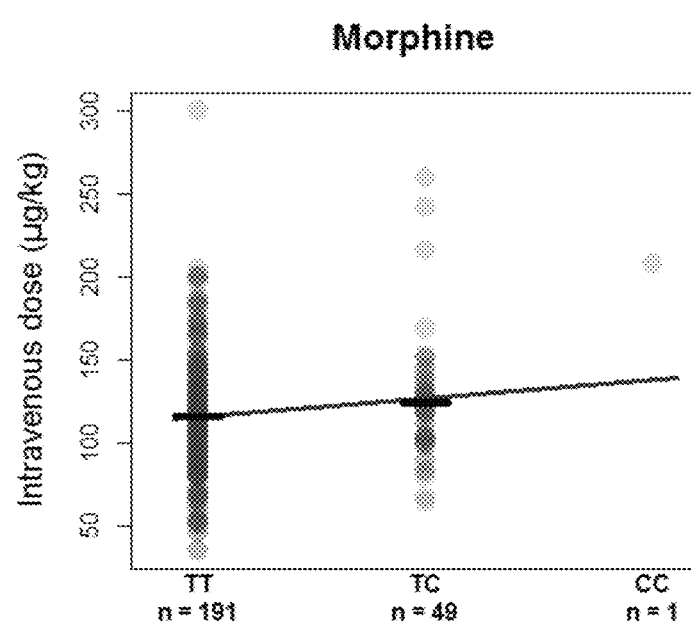
FIG. 3 shows morphine doses stratified by rs73568641 genotype in pediatric African-American (AA) surgical patients. Intravenous morphine dose is shown in micrograms/kilogram (µg/kg). Bars mark group means. Best fit line is shown.

Recently reviewed[43] candidate single nucleotide polymorphisms in the primary methadone metabolizing enzymes were tested for association with methadone dose in the Yale-Penn opioid dependence (OD) sample if genotype calls were available. Standard error (SE), reference single nucleotide polymorphism (SNP) cluster identification (RSID).
Methadone Dose-Associated SNP rs73568641 Also Associates with Morphine Dose in the CHOP Pediatric Surgical Patients Whether the implicated SNP upstream of OPRM1 also influences sensitivity to the analgesic effects of opioids was investigated. Because the observed association between rs73568641 and methadone dose was evident only in AAs, the effect of rs73568641 was examined in an independent AA sample. The only apparent published GWAS of opioid dosage in AAs[40] examined intravenous morphine doses in AA pediatric patients recovering from tonsillectomy and adenoidectomy. In these AA subjects (dose mean (SD)= 118.6 micrograms/kilogram (μg/kg) (39.8 μg/kg)), rs73568641-C was associated with a higher required morphine dose (n=241, β=11.6 μg/kg, standard error (SE)=5.6 μg/kg, two-tailed $P=3.9 \times 10^{-2}$), the same effect direction as for methadone dose (FIG. 3). In EA patients from the CHOP sample (dose mean (SD)=132.4 μg/kg (40.9 μg/kg)), no association between rs73568641-C and morphine dose was present (n=277, P=0.33). These consistent results across independent samples indicate that the effects of the locus are apparent in African-ancestry but not European-ancestry populations (no other populations were tested).
Opioid Analgesic Dose Genetic Score (GS) Associates with Higher Methadone Dose in the Yale-Penn OD Sample Prior GWASs have identified several top SNPs that, while not reaching genome-wide significance, associated in a replicable way to higher opioid analgesic dose, and implicated genes CREB1, TAOK3, and TRPC3.[40,44,45] A genetic score (GS) calculated using these dose-increasing alleles was associated with higher methadone dose, and the relationship was more evident in AAs than EAs (AA: n=383, two-tailed $P=6.6 \times 10^{-4}$; EA: n=1,027, two-tailed $P=8.0 \times 10^{-2}$; meta-analysis $P=1.3 \times 10^{-3}$).

As shown herein, individuals belonging to different population groups may respond differently to opioids, possibly due to genetic factors.[62] In a prior OD GWAS,[24] different results for AAs and EAs were reported, with the most significant results (which did not include any markers near OPRM1) in AAs. Similarly, in the present study, the association between rs73568641-C and higher opioid dose was specific to AAs for both methadone and morphine, and the GS association signal was stronger in methadone-treated AAs than EAs. GWAS SNPs often tag many common variants, as is the case here (FIG. 1), and population-specific GWAS findings[63] may be related to linkage disequilibrium between commons SNPs and population-specific rare functional variants.[64] Whole genome sequencing approaches and larger samples can be used to interrogate fully variation across the allele frequency spectrum in multiple ancestry groups. Some polymorphisms may have phenotypic effects only when population-specific variants in the region are present to interact with them (epistasis), for example.[65]

Clinicians tend to prescribe lower doses of opioids to minority patients,[66] including minority children,[67] and OD treatment programs serving a higher proportion of AA patients are more likely to report under-dosing of methadone.[50] In the present data, observed lower opioid doses for AAs compared to EAs were observed (methadone: t-test P<0.001; morphine: t-test P<0.001). If EA subjects are dosed more liberally than AA subjects, who receive doses closer to the therapeutic minimum or are undertreated, objective markers to guide dosing could serve to mitigate under-dosing and consequent health disparities.
Materials and Methods
Recruitment and Assessment of Subjects with Opioid Dependence (OD)

Details on the Yale-Penn sample have been published previousl[24,27,28]. Briefly, adults with a history of dependence on alcohol, opioids, or cocaine and controls were recruited at five sites in the Eastern United States, primarily via community advertisements and word of mouth, as part of ongoing studies of drug and alcohol dependence genetics. The sample consisted of small nuclear families with affected and unaffected members (originally collected for linkage studies), and unrelated cases and controls. Exclusion criteria included a history of psychotic disorders (schizophrenia, bipolar disorder), serious head injury, or inability to read English at a sixth-grade level. Subjects gave written informed consent as approved by the Institutional Review Board (IRB) at each site, and certificates of confidentiality were obtained from the National Institute on Drug Abuse and the National Institute on Alcohol Abuse and Alcoholism. In-person interviews were conducted by trained interviewers using the Semi-Structured Assessment for Drug Dependence and Alcoholism (SSADDA), which is a comprehensive polydiagnostic instrument that yields reliable information on major DSM-IV diagnoses and diagnostic criteria (available at nidagenetics.org/filebrowser/download/3765).[29,30] The SSADDA covers psychiatric and substance use disorders, as well as social and medical history and demographic information.

Methadone dose Genome-Wide Association Study (GWAS) in Methadone-Treated OD Subjects DNA from study participants was extracted from blood, saliva, or immortalized cell lines. Subjects were genotyped on either the Illumina HumanOmni1-Quad_v1.0 microarray, or the Illumina Human Core Exome microarray. Details on genotyping and data cleaning procedures have been described previously.[24,27,28] The present study included unrelated probands who were either self-reported African-Americans (AAs) or European-Americans (EAs), with population outliers removed based on principal component analysis (PCA) of genotype data.[31,32] The Human Core Exome microarray contains both exome-focused SNP content and tagging SNPs for genome-wide imputation, and additional details about the application of quality control procedures to the Human Core Exome microarray data are provided below. As previously described, imputation of genotype data was performed from the 1000 Genomes Project Phase 1 reference panel using Impute2.[33-35]

All subjects selected for the GWAS met criteria for DSM-IV OD. Subjects who had been treated with methadone were asked the following question: "When you were taking methadone, what was your usual dosage?" Data on daily methadone dose were available for a total of 383 AAs and 1,027 EAs. Methadone dose data, in milligrams (mg), were transformed to normality with an inverse-normal transformation,[36] and used as the dependent variable in the GWAS. The GWAS was carried out with Plink v.107[37], adjusting for age, sex, weight, and 10 principal components (PCs). Within each of the two ancestry groups (EA and AA), separate analyses were run on subjects genotyped on the HumanOmni1-Quadv1.0 and Human Core Exome microarrays. SNPs were filtered out if the minor allele frequency (MAF) was <5%, or if the imputation INFO score was <0.7. Meta-analyses were then performed within ancestry groups using METAL, which was also used to remove SNPs with heterogeneous effect estimates across the two microarrays, and to adjust summary statistics based on the genomic inflation factor ($\lambda$)[38] LocusZoom was used for regional association plot generation.[39] The cutoff for genome-wide significance was defined using the criterion of $P=5.0\times10^{-8}$.

Genotyping with Illumina Human Core Exome Microarray and Quality Control

Genotypes were called with Gencall, and a 2% cutoff was imposed for both subject call rate and autosomal marker call rate. SNPs were then initially filtered based on a minor allele frequency (MAF) cutoff of 0.03 and Hardy-Weinberg Equilibrium (HWE) $P<1\times10^{-6}$.

After combining genotype data from the Human Core Exome microarray and the 1000 Genomes (1 KG) project,[33] k-means clustering was used to divide the sample into two clusters containing mostly European-Americans (EAs) or African-Americans (AAs), respectively. Within each cluster, heterozygosity outliers greater than 3 standard deviations from the mean were removed. Next, Zcall was applied to the data,[76] followed by removal of all markers previously flagged for missingness using Gencall genotype calls, as well as monomorphic markers and samples flagged for missingness. Then, prior to imputation, markers with MAF<0.01%, A/T and G/C markers, markers with HWE $P<1\times10^{-8}$, and indels were removed. Imputation from 1KG was carried out as described previously.[24, 27-28, 34, 35] Before further analysis, subjects were removed if identity-by-descent (IBD) estimates showed unexpectedly high genetic similarity for subjects not known to be related, or low genetic similarity for subjects ascertained as members of a family. Subjects were also removed if they had already been genotyped on the Illumina HumanOmni1-Quadv1.0 microarray, or were outliers based on the first 10 PCs in their assigned cluster, and unrelated probands with self-reported EA or AA ancestry were retained.

Intravenous Morphine Dose in Opioid-Naïve Pediatric Surgery Patients

Children 4-18 years old who received intravenous morphine during a tonsillectomy and adenoidectomy at the Children's Hospital of Philadelphia (CHOP) were identified using the Anesthesia Information Management system (CompuRecord, Phillips Medical Systems, Andover, Mass.). All surgeries were performed between Nov. 1, 2001 and Dec. 1, 2009. Exclusion criteria included obstructive sleep apnea, a combination of tonsillectomy and adenoidectomy with another procedure, or administration of other intraoperative anesthetics. While recovering in the Post-anesthesia Care Unit (PACU), children received additional intravenous morphine (in 25-50 µg/kg increments) to control their pain. The CHOP IRB approved collection of these data.

A subset of the patients meeting the above inclusion criteria had previously been consented for genomic study and genotyped (on either the Illumina Human-Hap550 or Illumina Human610-Quad microarray) by the Center for Applied Genomics at CHOP, as approved by the CHOP IRB. Sample details and quality control of phenotype and genotype data have been described previously.[40] The 1000 Genomes Project reference panel and Impute2[33-35] were used to impute the top methadone dose GWAS SNP. In this sample, total intravenous morphine dose (µg/kg) was treated as a quantitative trait, and SNPTEST V2[41] was used to test for an association with the SNP. The same statistical model previously developed for this sample was used, which included age, body mass index, and American Society of Anesthesiologists physical status as covariates.[40]

Opioid Analgesic Dose Genetic Score (GS) in an Opioid Dependence (OD) Sample

The literature on opioid sensitivity single nucleotide polymorphisms (SNPs) was reviewed. Because none of the published SNPs met criteria for genome-wide significance, SNPs were selected based on study methodology and whether the findings were replicated. A SNP was considered to have been validated if its association with opioid dose was initially discovered via GWAS, and if it then showed the same effect in a non-overlapping sample. Three SNPs met these criteria. Rs795484 in TAOK3 was described in a previous study of intravenous morphine dose.[8] Rs795484 was associated in a replicable way and most significantly with morphine dose in EAs, and also with documented pain scores in morphine-treated EAs and AAs. Rs2952768, adjacent to CREB1, was associated with fentanyl dose in Japanese patients recovering from cosmetic orthognathic surgery, and with analgesic dose in a separate sample of Japanese abdominal surgery patients.[44] Rs1465040, upstream of TRPC3, was identified in the same samples as rs2952768.

For all three opioid analgesic dose-associated SNPs, the minor allele (rs1465040-T, rs2952768-C, and rs795484-A) was associated with higher opioid dose in the original study.[77, 44, 45] A GS was calculated for every subject in the methadone-treated sample. For each individual, the imputed minor allele dosage for each of the three dose-increasing SNPs was summed. Adjusting for the same covariates used in the GWAS, the GS was tested in a sample of the present disclosure for association with methadone dose. The GS was first analyzed separately in AAs and EAs, followed by meta-analysis.

Statistical Analysis

Phenotype data were prepared for GWAS using the R statistical computing environment,[42] which was also used to generate phenotype data summary statistics (means, standard deviations).

REFERENCES

1. Frieden T R, Houry D. Reducing the Risks of Relief—The CDC Opioid-Prescribing Guideline. *N Engl J Med.* 2016; 374(16):1501-1504.
2. Okie S. A flood of opioids, a rising tide of deaths. *N Engl J Med.* 2010; 363(21):1981-1985.
3. Dowell D, Haegerich T M, Chou R. CDC Guideline for Prescribing Opioids for Chronic Pain—United States, 2016. *JAMA.* 2016; 315(15):1624-1645.
4. Dole V P. Implications of methadone maintenance for theories of narcotic addiction. *JAMA.* 1988; 260(20): 3025-3029.
5. Dole V P, Nyswander M. A MEDICAL TREATMENT FOR DIACETYLMORPHINE (HEROIN) ADDICTION. A CLINICAL TRIAL WITH METHADONE HYDROCHLORIDE. *JAMA: the journal of the American Medical Association.* 1965; 193:646-650.
6. Kreek M J, LaForge K S, Butelman E. Pharmacotherapy of addictions. *Nat Rev Drug Discov.* 2002; 1(9):710-726.
7. Harding-Pink D. Methadone: one person's maintenance dose is another's poison. *Lancet.* 1993; 341(8846):665-666.
8. Maxwell S, Shinderman M S. Optimizing long-term response to methadone maintenance treatment: a 152-week follow-up using higher-dose methadone. *J Addict Dis.* 2002; 21(3):1-12.
9. Berridge V. Heroin prescription and history. *N Engl J Med.* 2009; 361(8):820-821.
10. Courtwright D T. Preventing and Treating Narcotic Addiction—Century of Federal Drug Control. *N Engl J Med.* 2015; 373(22):2095-2097.
11. Substance Abuse and Mental Health Services Administration CfBHSaQ. *The N-SSATS Report: Trends in the Use of Methadone and Buprenorphine at Substance Abuse Treatment Facilities:* 2003 to 2011. Rockville, Md. 2013.
12. Crist R C, Berrettini W H. Pharmacogenetics of OPRM1. *Pharmacol Biochem Behav.* 2014; 123:25-33.
13. Zhang H, Luo X, Kranzler H R, et al. Association between two mu-opioid receptor gene (OPRM1) haplotype blocks and drug or alcohol dependence. *Hum Mol Genet.* 2006; 15(6):807-819.
14. Hung C C, Chiou M H, Huang B H, et al. Impact of genetic polymorphisms in ABCB1, CYP2B6, OPRM1, ANKK1 and DRD2 genes on methadone therapy in Han Chinese patients. *Pharmacogenomics.* 2011; 12(11): 1525-1533.
15. Oslin D W, Leong S H, Lynch K G, et al. Naltrexone vs Placebo for the Treatment of Alcohol Dependence: A Randomized Clinical Trial. *JAMA Psychiatry.* 2015; 72(5):430-437.
16. Gelernter J, Gueorguieva R, Kranzler H R, et al. Opioid receptor gene (OPRM1, OPRK1, and OPRD1) variants and response to naltrexone treatment for alcohol dependence: results from the VA Cooperative Study. *Alcohol Clin Exp Res.* 2007; 31(4):555-563.
17. Schwantes-An T H, Zhang J, Chen L S, et al. Association of the OPRM1 Variant rs1799971 (A118G) with Non-Specific Liability to Substance Dependence in a Collaborative de novo Meta-Analysis of European-Ancestry Cohorts. *Behav Genet.* 2016; 46(2):151-169.
18. Hancock D B, Levy J L, Gaddis N C, et al. Cis-Expression Quantitative Trait Loci Mapping Reveals Replicable Associations with Heroin Addiction in OPRM1. *Biol Psychiatry.* 2015; 78(7):474-484.
19. Kharasch E D, Regina K J, Blood J, Friedel C. Methadone Pharmacogenetics: CYP2B6 Polymorphisms Determine Plasma Concentrations, Clearance, and Metabolism. *Anesthesiology.* 2015; 123(5):1142-1153.
20. Eap C B, Broly F, Mino A, et al. Cytochrome P450 2D6 genotype and methadone steady-state concentrations. *J Clin Psychopharmacol.* 2001; 21(2):229-234.
21. Crettol S, Déglon J J, Besson J, et al. ABCB1 and cytochrome P450 genotypes and phenotypes: influence on methadone plasma levels and response to treatment. *Clin Pharmacol Ther.* 2006; 80(6):668-681.
22. Leavitt S B, Shinderman M, Maxwell S, Eap C B, Paris P. When "enough" is not enough: new perspectives on optimal methadone maintenance dose. *Mt Sinai J Med.* 2000; 67(5-6):404-411.
23. Dennis B B, Bawor M, Thabane L, Sohani Z, Samaan Z. Impact of ABCB1 and CYP2B6 genetic polymorphisms on methadone metabolism, dose and treatment response in patients with opioid addiction: a systematic review and meta-analysis. *PLoS One.* 2014; 9(1):e86114.
24. Gelernter J, Kranzler H R, Sherva R, et al. Genome-wide association study of opioid dependence: multiple associations mapped to calcium and potassium pathways. *Biological psychiatry.* 2014; 76(1):66-74.
25. Nelson E C, Agrawal A, Heath A C, et al. Evidence of CNIH3 involvement in opioid dependence. *Molecular psychiatry.* 2016; 21(5):608-614.
26. Bosker F J, Hartman C A, Nolte I M, et al. Poor replication of candidate genes for major depressive disorder using genome-wide association data. *Mol Psychiatry.* 2011; 16(5):516-532.
27. Gelernter J, Kranzler H R, Sherva R, et al. Genome-wide association study of alcohol dependence: significant findings in African- and European-Americans including novel risk loci. *Molecular psychiatry.* 2014; 19(1):41-49.
28. Gelernter J, Sherva R, Koesterer R, et al. Genome-wide association study of cocaine dependence and related traits: FAM53B identified as a risk gene. *Molecular psychiatry.* 2014; 19(6):717-723.
29. Pierucci-Lagha A, Gelernter J, Feinn R, et al. Diagnostic reliability of the Semi-structured Assessment for Drug Dependence and Alcoholism (SSADDA). *Drug and Alcohol Dependence.* 2005; 80(3):303-312.
30. Pierucci-Lagha A, Gelernter J, Chan G, et al. Reliability of DSM-IV diagnostic criteria using the semi-structured assessment for drug dependence and alcoholism (SSADDA). *Drug and alcohol dependence.* 2007; 91(1): 85-90.

31. Price A L, Patterson N J, Plenge R M, Weinblatt M E, Shadick N A, Reich D. Principal components analysis corrects for stratification in genome-wide association studies. *Nature genetics.* 2006; 38(8):904-909.
32. Patterson N, Price A L, Reich D. Population structure and eigenanalysis. *PLoS genetics.* 2006; 2(12):e190.
33. Abecasis G R, Auton A, Brooks L D, et al. An integrated map of genetic variation from 1,092 human genomes. *Nature.* 2012; 491(7422):56-65.
34. Howie B N, Donnelly P, Marchini J. A Flexible and Accurate Genotype Imputation Method for the Next Generation of Genome-Wide Association Studies. *PLoS Genetics.* 2009; 5(6):e1000529.
35. Delaneau O, Marchini J, Zagury J. A linear complexity phasing method for thousands of genomes. *Nature Methods.* 2012; 9(2):179-181.
36. Locke A E, Kahali B, Berndt S I, et al. Genetic studies of body mass index yield new insights for obesity biology. *Nature.* 2015; 518(7538):197-206.
37. Purcell S, Neale B, Todd-Brown K, et al. PLINK: A Tool Set for Whole-Genome Association and Population-Based Linkage Analyses. *The American Journal of Human Genetics.* 2007; 81(3):559-575.
38. Willer C J, Li Y, Abecasis G R. METAL: fast and efficient meta-analysis of genomewide association scans. *Bioinformatics* (Oxford, England). 2010; 26(17):2190-2191.
39. Pruim R J, Welch R P, Sanna S, et al. LocusZoom: regional visualization of genome-wide association scan results. *Bioinformatics.* 2010; 26(18):2336-2337.
40. Cook-Sather S D, Li J, Goebel T K, Sussman E M, Rehman M A, Hakonarson H. TAOK3, a novel genome-wide association study locus associated with morphine requirement and postoperative pain in a retrospective pediatric day surgery population. *Pain.* 2014; 155(9):1773-1783.
41. Marchini J, Howie B, Myers S, McVean G, Donnelly P. A new multipoint method for genome-wide association studies by imputation of genotypes. *Nature Genetics.* 2007; 39(7):906-913.
42. R Core Team. R: *A language and environment for statistical computing.* Vienna, Austria: R Foundation for Statistical Computing; 2016.
43. Somogyi A A, Barratt D T, Ali R L, Coller J K. Pharmacogenomics of methadone maintenance treatment. *Pharmacogenomics.* 2014; 15(7):1007-1027.
44. Nishizawa D, Fukuda K, Kasai S, et al. Genome-wide association study identifies a potent locus associated with human opioid sensitivity. *Molecular psychiatry.* 2014; 19(1):55-62.
45. Aoki Y, Nishizawa D, Hasegawa J, et al. Association between the rs1465040 single-nucleotide polymorphism close to the transient receptor potential subfamily C member 3 (TRPC3) gene and postoperative analgesic requirements. *J Pharmacol Sci.* 2015; 127(3):391-393.
46. Vestal C. In Fighting An Opioid Epidemic, Medication-Assisted Treatment Is Effective But Underused. *Health Aff (Millwood).* 2016; 35(6):1052-1057.
47. Mattick R P, Breen C, Kimber J, Davoli M. Buprenorphine maintenance versus placebo or methadone maintenance for opioid dependence. *Cochrane Database Syst Rev.* 2014; 2:CD002207.
48. Johnson R E, Chutuape M A, Strain E C, Walsh S L, Stitzer M L, Bigelow G E. A comparison of levomethadyl acetate, buprenorphine, and methadone for opioid dependence. *N Engl J Med.* 2000; 343(18):1290-1297.
49. Strain E C, Bigelow G E, Liebson I A, Stitzer M L. Moderate-vs high-dose methadone in the treatment of opioid dependence: a randomized trial. *JAMA.* 1999; 281(11):1000-1005.
50. D'Aunno T, Pollack H A, Frimpong J A, Wuchiett D. Evidence-based treatment for opioid disorders: a 23-year national study of methadone dose levels. *J Subst Abuse Treat.* 2014; 47(4):245-250.
51. Bell J R, Butler B, Lawrance A, Batey R, Salmelainen P. Comparing overdose mortality associated with methadone and buprenorphine treatment. *Drug Alcohol Depend.* 2009; 104(1-2):73-77.
52. Angst M S, Phillips N G, Drover D R, et al. Pain sensitivity and opioid analgesia: a pharmacogenomic twin study. *Pain.* 2012; 153(7):1397-1409.
53. Williams J T, Ingram S L, Henderson G, et al. Regulation of μ-opioid receptors: desensitization, phosphorylation, internalization, and tolerance. *Pharmacol Rev.* 2013; 65(1):223-254.
54. Yang H C, Chu S K, Huang C L, et al. Genome-Wide Pharmacogenomic Study on Methadone Maintenance Treatment Identifies SNP rs17180299 and Multiple Haplotypes on CYP2B6, SPON1, and GSG1L Associated with Plasma Concentrations of Methadone R- and S-enantiomers in Heroin-Dependent Patients. *PLoS Genet.* 2016; 12(3):e1005910.
55. Wang J S, DeVane C L. Involvement of CYP3A4, CYP2C8, and CYP2D6 in the metabolism of (R)- and (S)-methadone in vitro. *Drug Metab Dispos.* 2003; 31(6):742-747.
56. Coller J K, Joergensen C, Foster D J, et al. Lack of influence of CYP2D6 genotype on the clearance of (R)-, (S)- and racemic-methadone. *Int J Clin Pharmacol Ther.* 2007; 45(7):410-417.
57. Fonseca F, de la Torre R, Díaz L, et al. Contribution of cytochrome P450 and ABCB1 genetic variability on methadone pharmacokinetics, dose requirements, and response. *PLoS One.* 2011; 6(5):e19527.
58. Siegle I, Fritz P, Eckhardt K, Zanger U M, Eichelbaum M. Cellular localization and regional distribution of CYP2D6 mRNA and protein expression in human brain. *Pharmacogenetics.* 2001; 11(3):237-245.
59. Britto M R, Wedlund P J. Cytochrome P-450 in the brain. Potential evolutionary and therapeutic relevance of localization of drug-metabolizing enzymes. *Drug Metab Dispos.* 1992; 20(3):446-450.
60. Levran O, Peles E, Hamon S, Randesi M, Adelson M, Kreek M J. CYP2B6 SNPs are associated with methadone dose required for effective treatment of opioid addiction. *Addict Biol.* 2013; 18(4):709-716.
61. Kagimoto M, Heim M, Kagimoto K, Zeugin T, Meyer U A. Multiple mutations of the human cytochrome P450IID6 gene (CYP2D6) in poor metabolizers of debrisoquine. Study of the functional significance of individual mutations by expression of chimeric genes. J Biol Chem. 1990; 265(28):17209-17214.
62. Zhou H H, Sheller J R, Nu H, Wood M, Wood A J. Ethnic differences in response to morphine. *Clin Pharmacol Ther.* 1993; 54(5):507-513.
63. CONVERGE consortium. Sparse whole-genome sequencing identifies two loci for major depressive disorder. *Nature.* 2015; 523(7562):588-591.
64. Dickson S P, Wang K, Krantz I, Hakonarson H, Goldstein D B. Rare Variants Create Synthetic Genome-Wide Associations. *PLoS Biology.* 2010; 8(1):e1000294.

65. Polimanti R, Yang C, Zhao H, Gelernter J. Dissecting ancestry genomic background in substance dependence genome-wide association studies. *Pharmacogenomics.* 2015; 16(13):1487-1498.
66. Pletcher M J, Kertesz S G, Kohn M A, Gonzales R. Trends in opioid prescribing by race/ethnicity for patients seeking care in U.S. emergency departments. *JAMA.* 2008; 299(1):70-78.
67. Goyal M K, Kuppermann N, Cleary S D, Teach S J, Chamberlain J M. Racial Disparities in Pain Management of Children With Appendicitis in Emergency Departments. *JAMA Pediatr.* 2015; 169(11):996-1002.
68. Daly A K. Genome-wide association studies in pharmacogenomics. *Nat Rev Genet.* 2010; 11(4):241-246.
69. Mieda T, Nishizawa D, Nakagawa H, et al. Genome-wide association study identifies candidate loci associated with postoperative fentanyl requirements after laparoscopic-assisted colectomy. *Pharmacogenomics.* 2016; 17(2):133-145.
70. Langendam M W, van Haastrecht H J, van Ameijden E J. The validity of drug users' self-reports in a non-treatment setting: prevalence and predictors of incorrect reporting methadone treatment modalities. *Int J Epidemiol.* 1999; 28(3):514-520.
71. Cooper G M, Johnson J A, Langaee T Y, et al. A genome-wide scan for common genetic variants with a large influence on warfarin maintenance dose. *Blood.* 2008; 112(4):1022-1027.
72. Zineh I, Pacanowski M, Woodcock J. Pharmacogenetics and coumarin dosing—recalibrating expectations. *N Engl J Med.* 2013; 369(24):2273-2275.
73. Kimmel S E, French B, Kasner S E, et al. A pharmacogenetic versus a clinical algorithm for warfarin dosing. *N Engl J Med.* 2013; 369(24):2283-2293.
74. Verhoef T I, Ragia G, de Boer A, et al. A randomized trial of genotype-guided dosing of acenocoumarol and phenprocoumon. *N Engl J Med.* 2013; 369(24):2304-2312.
75. Pirmohamed M, Burnside G, Eriksson N, et al. A randomized trial of genotype-guided dosing of warfarin. *N Engl J Med.* 2013; 369(24):2294-2303.
76. Goldstein J I, Crenshaw A, Carey J, et al. zCall: a rare variant caller for array-based genotyping: genetics and population analysis. *Bioinformatics.* 2012; 28(19):2543-2545.
77. Cook-Sather S D, Li J, Goebel T K, Sussman E M, Rehman M A, Hakonarson H. TAOK3, a novel genome-wide association study locus associated with morphine requirement and postoperative pain in a retrospective pediatric day surgery population. *Pain.* 2014; 155(9):1773-1783.
78. Pruitt K D, Brown G R, Hiatt S M, et al. RefSeq: an update on mammalian reference sequences. Nucleic Acids Res. 2014; 42(Database issue):D756-763.
79. Wang K, Li M, Hakonarson H. ANNOVAR: functional annotation of genetic variants from high-throughput sequencing data. Nucleic Acids Res. 2010; 38(16):e164.
80. Wang S C, Ho I K, Tsou H H, et al. CYP2B6 polymorphisms influence the plasma concentration and clearance of the methadone S-enantiomer. J Clin Psychopharmacol. 2011; 31(4):463-469.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A personalized method of treating a subject who is dependent on an opioid, the method comprising:
    (a) performing a genotypic analysis on a nucleic acid obtained from a subject dependent on an opioid to identify the presence or absence of at least one C allele of single nucleotide polymorphism (SNP) rs73568641 located on chromosome 6; and
    (b) administering to the subject an effective amount of methadone, wherein the effective amount is increased by about 20 milligrams (mg) per day for each C allele identified in the nucleic acid, relative to a standard therapeutic dose of methadone.

2. The method of claim 1 further comprising identifying in the nucleic acid the presence of at least one C allele of single nucleotide polymorphism (SNP) rs73568641 located on chromosome 6.

3. The method of claim 1, wherein the subject is an African-American subject.

4. The method of claim 1, wherein the subject is undergoing treatment for dependence on an opioid.

5. The method of claim 1, wherein the opioid is morphine, codeine, fentanyl, hydrocodone, hydromorphone or meperidine.

6. The method of claim 1, wherein the standard therapeutic dose of a μ-opioid receptor agonist, antagonist or mixed agonist/antagonist is 50-80 mg per day.

7. A personalized method of treating a subject who is having pain, the method comprising:
    (a) performing a genotypic analysis on a nucleic acid obtained from a subject having pain to identify the presence or absence of at least one C allele of single nucleotide polymorphism (SNP) rs73568641 located on chromosome 6; and
    (b) administering to the subject an effective amount of a μ-opioid receptor agonist, wherein the effective amount is increased by about 10 micrograms/kilogram (μg/kg) for each C allele identified in the nucleic acid, relative to a standard therapeutic dose of a μ-opioid receptor agonist, for treatment of pain, wherein the μ-opioid receptor agonist is morphine, codeine, fentanyl, hydrocodone, hydromorphone or meperidine.

8. The method of claim 7 further comprising identifying in the nucleic acid the presence of at least one C allele of single nucleotide polymorphism (SNP) rs73568641 located on chromosome 6.

9. The method of claim 7, wherein the subject is an African-American subject.

10. The method of claim 7, wherein the subject is a pediatric subject between the ages of 4 years and 18 years.

11. The method of claim 7, wherein the opioid is morphine.

12. The method of claim 7, wherein the standard therapeutic dose of a μ-opioid receptor agonist, antagonist or mixed agonist/antagonist is 100-130 μg/kg.

* * * * *